United States Patent
Bertolero et al.

(10) Patent No.: US 6,837,864 B1
(45) Date of Patent: Jan. 4, 2005

(54) MULTICHANNEL CATHETER WITH OBTURATOR

(75) Inventors: Arthur A. Bertolero, Danville, CA (US); Raymond S. Bertolero, Danville, CA (US); Jerome B. Riebman, Sunnyvale, CA (US)

(73) Assignee: Endoscopic Technologies, Inc., Danville, CA (US)

( * ) Notice: Subject to any disclaimer, the term of this patent is extended or adjusted under 35 U.S.C. 154(b) by 0 days.

(21) Appl. No.: 09/913,881

(22) PCT Filed: Feb. 18, 2000

(86) PCT No.: PCT/US00/04374

§ 371 (c)(1),
(2), (4) Date: Aug. 16, 2001

(87) PCT Pub. No.: WO00/48659

PCT Pub. Date: Aug. 24, 2000

Related U.S. Application Data

(60) Provisional application No. 60/120,038, filed on Feb. 19, 1999.

(51) Int. Cl.$^7$ ............................................. A61M 37/00
(52) U.S. Cl. ...................... 604/6.16; 604/4.01; 604/509
(58) Field of Search ............................... 604/4.01, 5.01, 604/6.11, 6.14, 6.16, 19, 48, 500, 506, 507, 508, 509, 93.01, 96.01, 97.01, 102.01, 102.03, 103.03, 103.07, 117, 131, 164.01, 164.02, 164.09, 164.13, 170.01, 170.02, 173, 264, 523, 532; 606/191, 192, 194

(56) References Cited

U.S. PATENT DOCUMENTS 5,226,427 A      7/1993  Buckberg et al.
5,437,290 A  *  8/1995  Bolger et al. ................ 128/898
5,542,925 A  *  8/1996  Orth ......................... 604/103.1
5,697,905 A  * 12/1997  d'Ambrosio .............. 604/96.01
5,755,687 A      5/1998  Donlon
5,766,151 A  *  6/1998  Valley et al. ........... 604/103.07
5,782,740 A  *  7/1998  Schneiderman ................ 600/1
5,807,328 A      9/1998  Briscoe
5,868,703 A  *  2/1999  Bertolero et al. ....... 604/102.01
5,928,181 A  *  7/1999  Coleman et al. ................ 604/8
6,117,105 A  *  9/2000  Bresnaham et al. ..... 604/96.01

* cited by examiner

Primary Examiner—Nicholas D. Lucchesi
Assistant Examiner—Jennifer J Maynard
(74) Attorney, Agent, or Firm—GSS Law Group; Gregory Scott Smith; Carol D. Titus

(57)     ABSTRACT

This invention is a multichannel catheter for extracorporeal circulation of blood to a patient undergoing cardiovascular treatments or surgery. The catheter has three independent channels, an obturator and an expandable balloon at one end of the catheter. The first channel is the largest and is of a size that allows for delivery of blood through outlet parts in the wall of the first channel to a patient in an amount sufficient to maintain the patient's metabolism and perfusion throughout the treatment or surgery. The obturator is longitudinally insertable into the first channel. A second channel, smaller than the first, is integrated into the wall of the first channel, and is suitable for delivering a biologically active fluid (e.g., for cardioplegia) to the heart and/or venting the left heart. A third channel, also smaller than the first, is integrated into the wall of the first channel, and suitable for delivering a fluid to the balloon for its expansion when positioned in the ascending aorta to occlude the flow of blood to the heart. The catheter provides an improved means of preparing for or performing cardiovascular surgery on a patient using a cardiopulmonary machine for extracorporeal circulation of blood. The catheter is particularly useful for cardiac surgery.

3 Claims, 14 Drawing Sheets

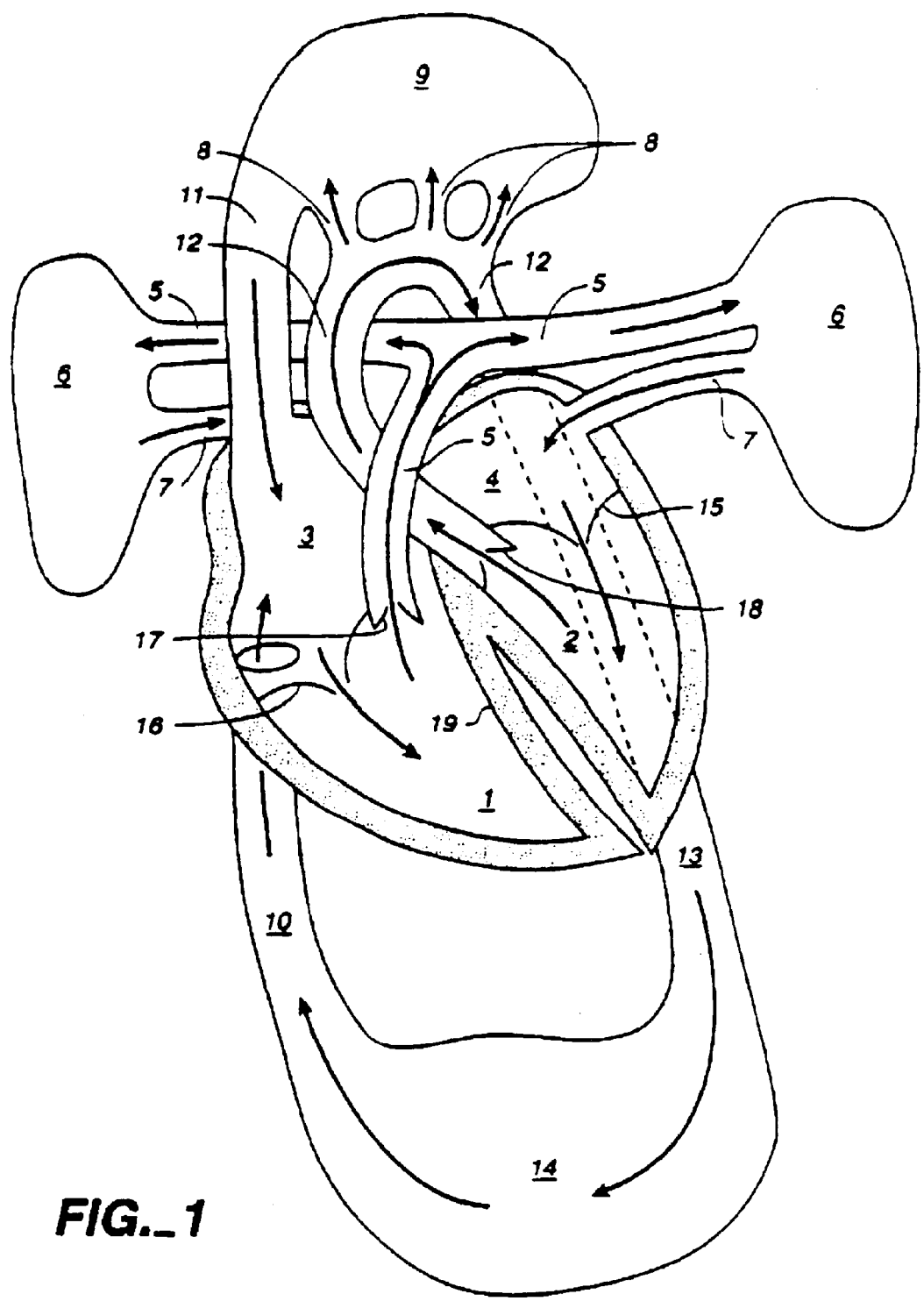
FIG._1

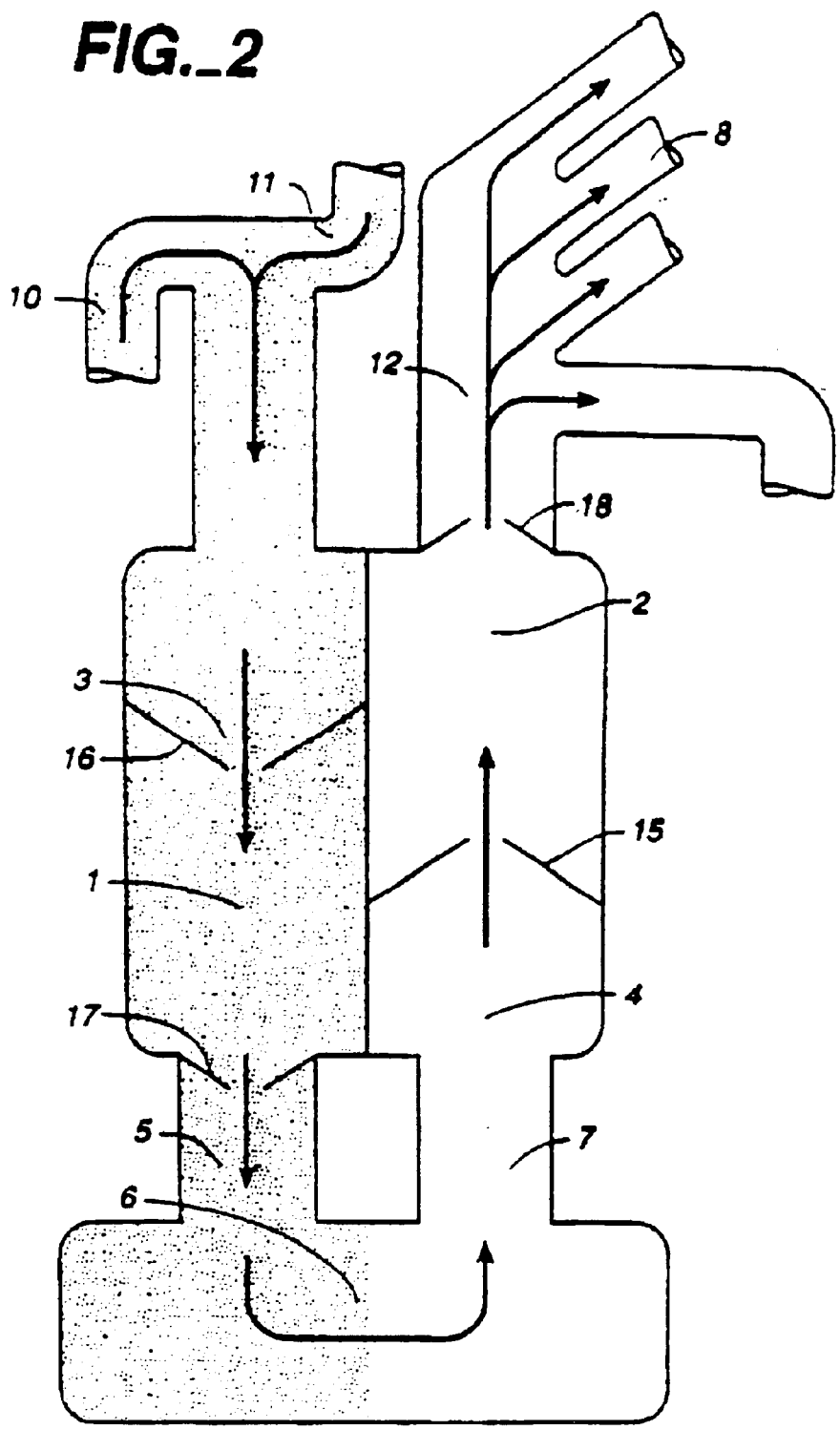
FIG._2

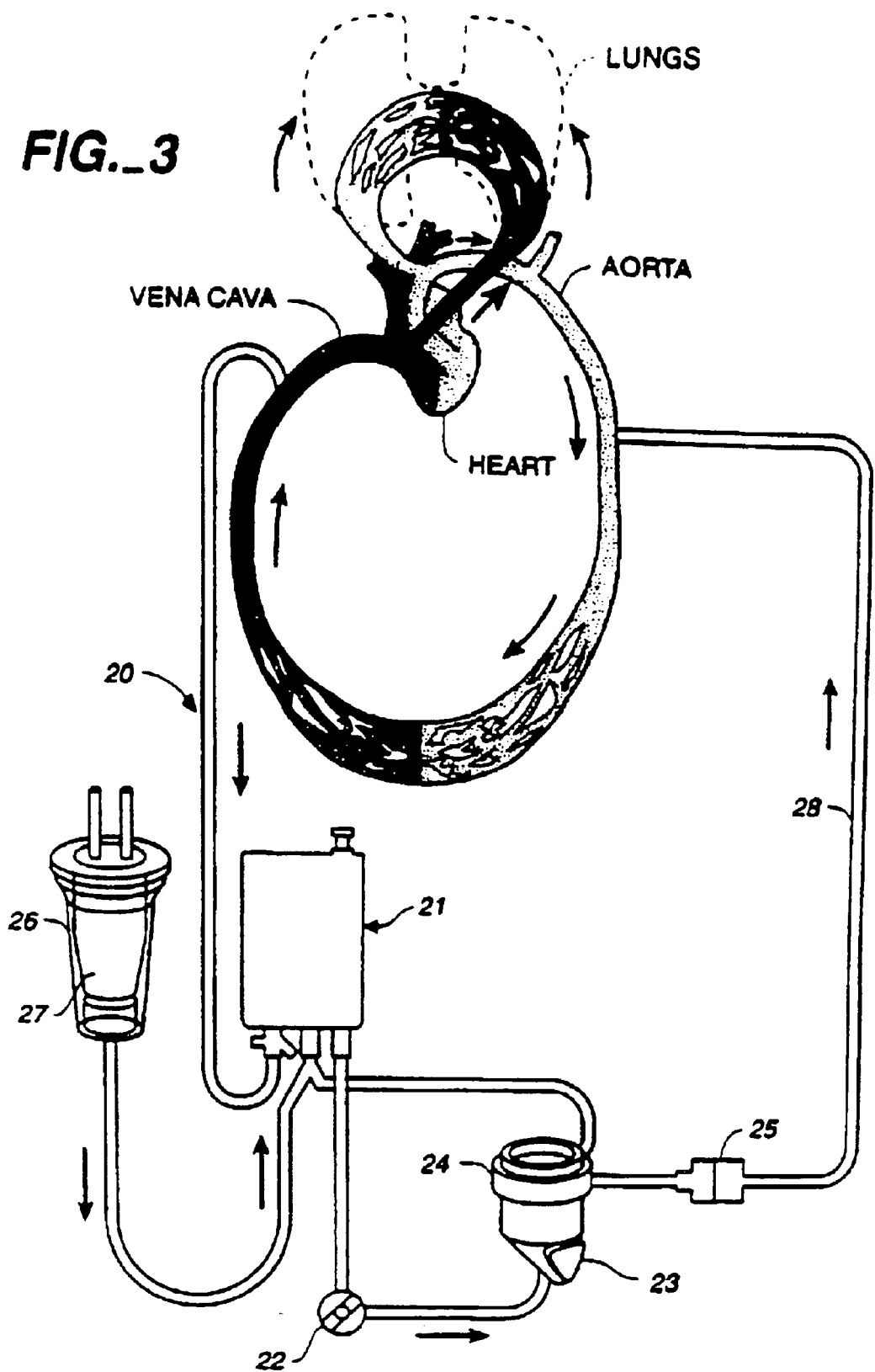

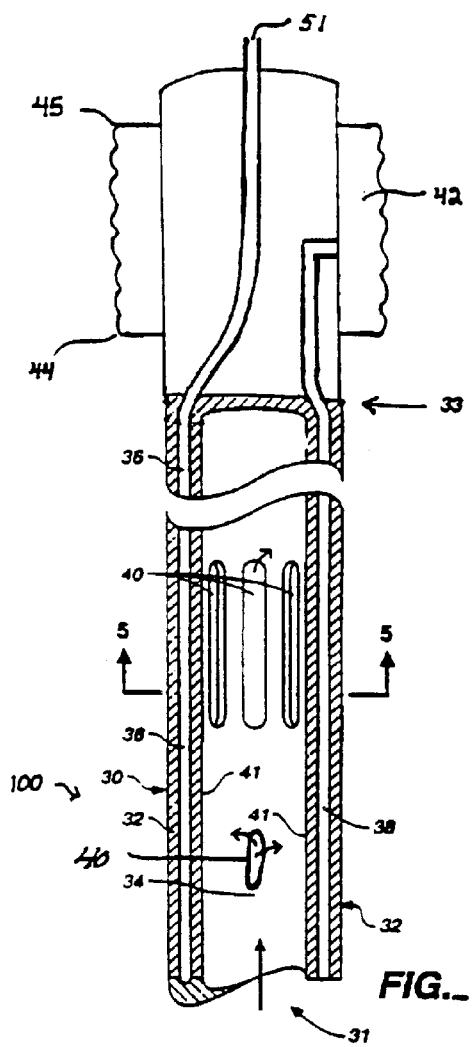
FIG._4
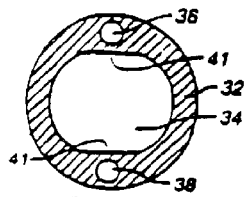
FIG._5A
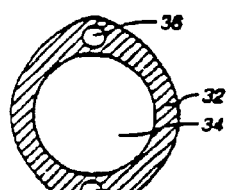
FIG._5B
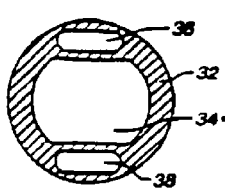
FIG._5C
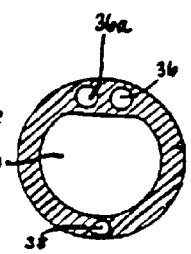
FIG._5D
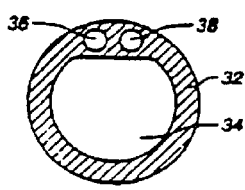
FIG._5E
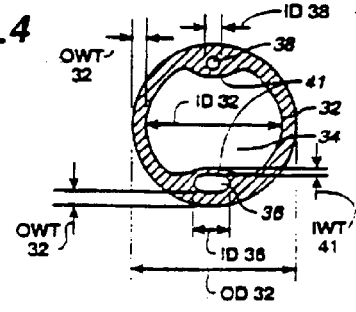
FIG._7

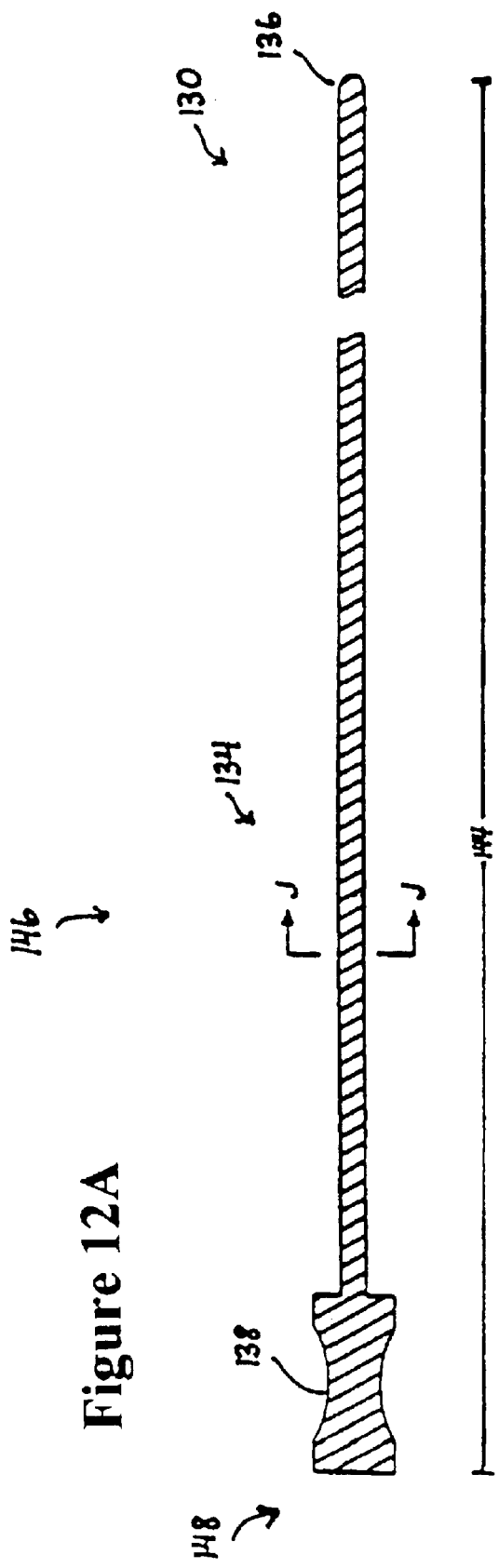
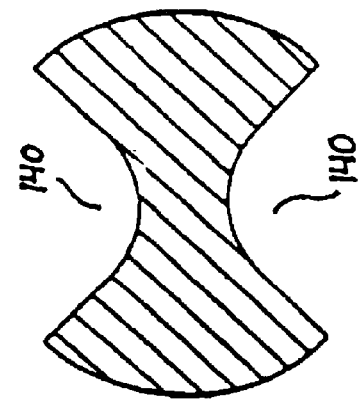
Figure 12A
Figure 12B

MULTICHANNEL CATHETER WITH OBTURATOR

RELATED U.S. APPLICATION DATA

This application claims the benefit of U.S. Provisional Application Ser. No. 60/120,038, filed Feb. 19, 1999.

BACKGROUND OF THE INVENTION

1. Field of the Invention

This invention relates to a multichannel catheter, i.e. a perfusion cannula, useful in arterial perfusion of the aorta, generally via a femoral artery for use in conjunction with cardiovascular examinations, treatments and surgery. It also relates to methods for making and using such a catheter.

2. Background of the Invention

To better understand the background and problems faced by those of skill in this area of technology it is useful to understand the basic workings of the heart and circulatory system. The following discussion refers to schematics of the heart shown in FIGS. 1 and 2. The human heart is a muscular pump having four separate cavities and a series of valves allowing blood to pass in one direction only. Mammals, including humans, have a double circulatory system. Blood that has released oxygen to the tissues 9 and 14 and has absorbed carbon dioxide from them (venous blood) is returned to the heart through the superior and the inferior venae cavae 11 and 10. This blood enters the right auricle 3, whose contractions cause the blood to pass through the tricuspid valve 16 in the right ventricle 1. The contractions of the right ventricle pass the blood through the pulmonary semilunar valves 17 and along the two pulmonary arteries 5 into the lungs 6. In the lungs, the blood is oxygenated and returns to the heart through the pulmonary veins 7 and thus enters the left auricle 4. This chamber contracts and passes the blood through the bicuspid, or mitral, valve 15 into the left ventricle 2, whose contractions force the blood through the aortic semilunar valve 18 into the aorta 12 and 13, which is the biggest artery of the body and to other parts of the body through, i.a., the great arteries 8. Thus the right side of the heart serves mainly to pump deoxygenated blood through the lungs, while the left side pumps oxygenated blood throughout the rest of the body. This is represented as a flow schematic in FIG. 2, where similar numbers refer to similar parts of the heart. The heart varies the output by varying the volume of blood admitted into the ventricles each time the latter are filled and also by varying the rate of contraction (faster or slower heartbeat). The left side of the heart (left auricle and ventricle) has to circulate the blood through all parts of the body, except the lungs, and has lip, thicker and more strongly muscular walls than the right side, which has to perform the pulmonary blood circulation only. For proper functioning, the left side and the fight side must be accurately interadjusted, both with regard to the contraction rate of the respective chambers and with regard to the output of blood. When functional disorders of the heart occur, it may be necessary to examine the heart to determine the problem and possibly perform surgery or provide treatment.

In performing examinations or treatments of a subject's heart, or performing surgery on the heart, it is often necessary to reduce the rate at which it normally beats or stop its beating completely. This allows a physician to observe, or operate on, the heart more easily. However, by reducing or stopping the heart rate (i.e. cardioplegia), blood will not be adequately circulated to the rest of the body. Thus, it is generally necessary to circulate the blood using some type of extracorporeal blood circulating means that regularly circulates oxygen-rich blood through the arteries, collects oxygen-depleted blood returning through the veins, enriches the oxygen-depleted blood with additional oxygen, then again circulates the oxygen-rich blood.

The types of examinations, treatments and operations that require some degree of cardioplegia or drug delivery and extracorporeal blood circulation include open heart surgery and less-invasive heart surgery to perform single or multiple coronary artery bypass operations, correct malfunctioning valves, etc. Others include, but are not limited to, myocardial revascularization, balloon angioplasty, correction of congenital defects, surgery of the thoracic aorta and great vessels, and neurosurgical procedures.

The extracorporeal blood circulation generally requires the use of some type of heart-lung machine, i.e. a cardiopulmonary machine. This has the threefold function of keeping the replacement blood in circulation by means of a pumping system, of enriching with fresh oxygen the blood of low oxygen content coming from the patient's body, and regulation of patient temperature. The system shown in FIG. 3 diagrammatically describes the manner in which such a machine works.

The venous blood, before it enters the right auricle of the heart is diverted into plastic tubes 20, generally by gravity flow. The tubes are positioned to receive the blood from the superior and inferior venae cavae (shown as 11 and 10 in FIG. 1). This blood, which has circulated through the body and consequently has a low oxygen content is collected in a reservoir 21. A blood pump 22 is used to pump the blood through a heat exchanger 23 and artificial lung 24. The heat exchanger 23 and artificial lung 24 may be one of several designs to regulate blood temperature and increase the oxygen content of the blood. Modern designs use advanced membrane technology to achieve the oxygenation, which is similar to the way red blood cells absorb oxygen from the human lung. The oxygenated blood then passes through a filter 25 and is returned to the patient. Losses of blood occurring during the course of the operation are compensated by an additional blood reservoir 26. Collected blood is passed through a defoamer 27 and is likewise passed to the reservoir 21, heat exchanger 23 and artificial lung 24. Before starting the cardiopulmonary bypass machine the extracorporeal circuit is filled with one or two liters of saline solution. In circulating the oxygenated blood to the body from filter 25, it can be pumped through a catheter 28 by inserting the catheter into the aorta or one of its major branches and pumping the blood through the catheter. However, when the heart is to be operated on, it must be free of blood and sometimes the heart beat must be reduced or stopped completely. Referring again to FIG. 1, blood is prevented from entering the heart by blocking the ascending aorta 12 near the semilunar valve 18 while at the same time preventing blood from entering the right auricle 3 by withdrawing blood through the superior vena cavae 11 and inferior vena cavae 10. Blocking the ascending aorta may be achieved by clamping or preferably by balloon blockage. At the same time that blood is prevented from flowing through the heart, a cardioplegia solution is administered locally to the heart to arrest the heart. Thus, there is a need for a device that allows a heart specialist to locally administer cardioplegia to the heart, block the flow of blood to the heart, while at the same time circulating oxygenated blood to the patient's body, particularly through the great arteries 8 in FIG. 1, to ensure all limbs and tissues remain undamaged during the heart examination or operation. Several devices are described in the literature to address the need for an appropriate device. One example is disclosed in U.S. Pat. No. 5,312,344 issued 17 May 1994 to Grinfeld et al.

Another example can be seen in U.S. Pat. No. 5,433,700, issued 19 Jul. 1995 to Peters. This patent describes a process for inducing cardioplegic arrest of a heart which comprises maintaining the patient's systemic circulation by peripheral cardiopulmonary bypass, occluding the ascending aorta through a percutaneously placed arterial balloon catheter, venting the left side of the heart, and introducing a cardioplegia agent into the coronary circulation. As part of the disclosure a multichannel catheter is disclosed which provides channels for the cardioplegia solution, a fluid transportation to inflate the balloon, a lumina for instrumentation and a separate catheter to deliver oxygenated blood to the body.

Another example of a device is found in U.S. Pat. No. 5,478,309, issued 26 Dec. 1995 to Sweezer et al. This is a rather complex device and system of venous perfusion and arterial perfusion catheters for use in obtaining total cardiopulmonary bypass support and isolation of the heart during the performance of heart surgery.

Another device is described in U.S. Pat. No. 5,458,574, issued 17 Oct. 1995 to Machold et al. It shows a multichannel catheter which has channels for fluid to blow up balloons for blocking the aorta, a channel for cardioplegia solution and a channel for instruments for examining the heart.

Still another patent, U.S. Pat. No. 5,452,733, issued 26 Sep. 1995 to Sterman et al.

Another patent application, PCT/US 94/09938, having international publication number WO95/08364, filed 1 Sep. 1994 in the name of Evard et al., describes an endovascular system for arresting the heart. PCT International Application number PCT/US 94/12986, published as Publication number WO95/15192, filed 10 Nov. 1994, in the name of Stevens et al., provides a description of a partitioning device that is coupled to an arterial bypass cannula U.S. Pat. No. 5,868,703, issued 9 Feb. 1999 (the '703 patent), discloses an improved device that aids a surgeon in performing open or closed heart surgery.

However, the design of the improved device has led to certain problems in the smooth operation of the device. For example, the design of the '703 device requires the presence of blood outlets strategically located along a portion of the multichannel catheter. When the distal tip of the device, which carries the balloon, is inserted into a femoral artery through a percutaneous opening, some of the blood portal will be located inside the artery (interior portals) while others will be temporarily located outside the artery (exterior portals). For a short period of time, blood, which flows in the artery will enter the catheter through the interior blood portal then exit through the exterior portals. This problem is solved by this invention through using an internal, slidable obturator in the blood flow channel to block both the interior & exterior portals during insertion of the multichannel catheter until all the portals are located within the artery. The obturator is then withdrawn to allow blood from a cardiopulmonary machine to be pumped through the blood flow channel of the multichannel catheter.

SUMMARY OF THE INVENTION

One aspect of this invention is a multichannel catheter useful for delivering extracorporeal blood to a mammal (particularly a human) by insertion into a blood vessel of the mammal. The catheter has a defined length with distal and proximal ends. The catheter has a central, first channel defined by a surrounding wall extending substantially the length of the catheter, which channel is closed at its distal end. A second channel (i) extends the entire length of the catheter parallel to the first channel but independent thereof, (ii) is integrated into the wall of the first channel, and (iii) is open at its distal end. In the wall of the catheter is at least one opening for the flow of blood communicating only with said first channel. Integrated into the distal end of the catheter between the opening for the flow of blood and the second channel distal opening is an inflatable bladder. A third channel (i) extends substantially the length of the catheter integrated into the wall of the first channel; (ii) being parallel to the first and second channels but independent thereof, and (iii) has a distal opening in fluid communication with the interior of the inflatable bladder. A solid flexible shaft Still another aspect of this invention is a process for preparing for cardiovascular surgery in a mammal. The process comprises (A) inserting into a femoral artery of the mammal the distal end of the catheter described above (and in greater detail hereinafter) with the flexible shaft slidingly engaged in the first channel to prevent backflow of blood, (B) positioning the catheter so that the inflatable bladder is located in the ascending aorta, and (C) removing the flexible shaft from the first channel to allow the first channel to be connected to a cardiopulmonary machine to pump blood into the first channel at the proximal end of the first channel. Other steps are also taken, as discussed hereinafter.

Another aspect of this invention is a process for preparing a multichannel catheter. The process comprises:

(A) extrusion molding a catheter having distal and proximal ends wherein the catheter comprises
  (1) a central, first channel extending substantially the length of the catheter and being defined by the wall of the catheter;
  (2) a second channel extending the entire length of the catheter, being integrated into the wall of the first channel;
  (3) a third channel extending substantially the length of the catheter parallel to the first and second channels but independent thereof and being integrated into the wall of the first channel and spaced from the second channel, (B) integrating an inflatable bladder into the distal end of the catheter so that a distal outlet of the third channel communicates with the interior of the bladder; and (C) slidingly inserting a flexible, shaft into the central first channel, wherein the shaft has a handle for positioning the shaft within the central channel.

Alternatively, the invention can be described as a multichannel catheter useful for extracorporeal circulation of the blood to a patient undergoing cardiovascular surgery. The catheter comprises at least three independent channels and an expandable balloon at one end of the catheter. The catheter has a first channel of a size to permit delivery of an amount of blood to the patient that is sufficient to support the patient metabolism and perfusion throughout the surgery. The first channel has at least one outlet port along at least a portion of the wall of the channel. A second channel, narrower than the first channel and integrated into the wall of the first channel, is present for at least for delivering cardioplegia solution to the heart or for venting the left heart. A third channel, also narrower than the first channel and integrated into the wall of the first channel, is suitable for delivery of fluid to the balloon for expansion when positioned in the ascending aorta to occlude the flow of blood. A flexible shaft is slidably inserted into the first channel of the catheter and has a handle located at the proximal end of the shaft for slidably positioning the shaft along the length of the first channel to block at least one outlet port in the wall of the catheter.

Another aspect of this invention is an obturator useful for slidably inserting into a blood-flow catheter, which oburator comprises a flexible shaft made of medical grade polymeric materials having a length of about 40 cm to about 120 cm, having a cross-sectional diameter of less than about 28.2 French, having a Durometer rating of about 40 A to about 90 A, and having a cross-sectional design to snugly and slidingly fit into a blood flow catheter channel to block the flow of blood through the channel.

Other aspects of the invention will be apparent to one of skill in the art upon reading the following specification and claims.

DESCRIPTION OF THE DRAWINGS

In the accompanying drawings:

FIG. 1 is a diagram of a mammal's heart and circulatory system showing the approximate configuration of the heart.

FIG. 2 is a schematic representative of how a mammalian heart works without regard to its configuration.

FIG. 3 is a schematic representation of how a cardiopulmonary machine works.

FIG. 4 is a longitudinal cross-section view of the proximal portion of the balloon catheter of the invention showing the interrelationship between the major parts of the proximal portion.

FIG. 5A is a perpendicular cross-section taken along line 5—5 of FIG. 4.

FIG. 5B shows a closely related configuration taken along line 5—5 of FIG. 4.

FIG. 5C shows a slight modification of the cross-section taken along the line 5—5 of FIG. 4.

FIGS. 5D and 5E show a slightly different modification of the cross-section taken along the line 5—5 of FIG. 4.

FIG. 7 shows a perpendicular cross-section taken along lines 5—5 of FIG. 4 and shows the size relationships between the various parts of the multi-channel catheter of this invention.

FIGS. 12A and 12B show a full length view of the obturator useful in this invention and a perpendicular cross-section taken along lines J—J of the full length obturator and shows the size relationships between the various parts of the obturator.

DETAILED DESCRIPTION OF PRESENTLY PREFERRED EMBODIMENTS

Figure 6B:
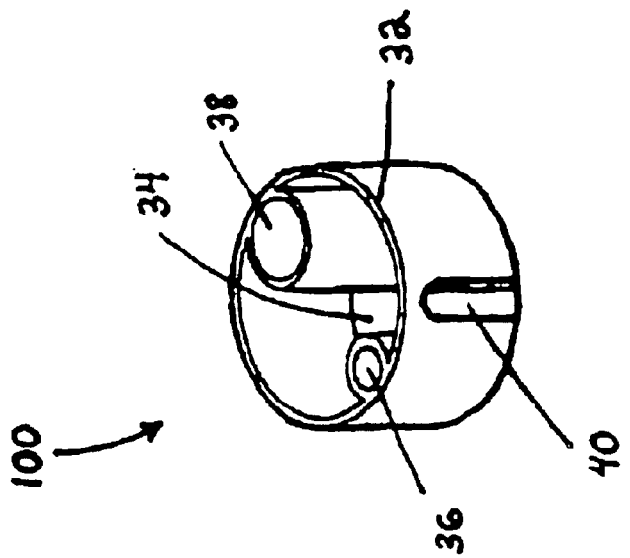
FIGS. 6A and 6B show a cross-section of the longitudinal axis of a slightly different configuration of the proximal portion of the multi-lumen catheter of this invention.

This invention is based on the discovery that an obturator, that is, a device used to block a longitudinal passageway, can be used to prevent blood leakage in certain blood delivery catheters. The invention has several aspects: (1) a multi-channel aortic balloon catheter in combination with an obturator; (2) the design of the obturator itself; (3) a process for using the combination of (1), above; and (4) a process for making the combination. Other aspects will be apparent to one of skill in the art upon further reading of the details of this specification.

Multi-Channel Catheter and Obturator

One aspect of this invention is a multichannel catheter (that includes an obturator) that is useful for delivering exracorporeal blood to a mammal (especially a human) in need thereof. The catheter allows a physician to deliver extracorporeal blood to the patient, occlude the flow of blood at the ascending aorta, deliver cardioplegia fluid to the heart, vent the left heart, and optionally monitor pressure and observe the internal workings of the aorta region.

The multichannel catheter is of a diameter size to be inserted into the aorta or one of its major branches (e.g. a femoral artery) and used in open chest surgery or in less invasive surgery. Alternatively, the catheter is used in open chest surgery and inserted by cannulation at the aorta or through one of the great arteries, e.g., the brachiocephalic artery. The design of the blood flow configuration will depend on where and how the catheter is to be inserted, as discussed hereinafter.

In general, the multichannel catheter of this invention comprises at least 3 passageways, with a large, central passageway to maximize the flow of oxygenated blood from a cardiopulmonary machine. It is desirable to maximize the flow of blood through the large channel while minimizing the outside diameter of the catheter and thus provide adequate systemic extracorporeal blood flow for the vast majority of patients in which the catheter is used. Of the available longitudinal passage space in the catheter of this invention, generally at least about 50% is allocated to this large passageway to maximize the flow. Preferably about 70% and more preferably about 90% of the available passageway volume, is used for the flow of perfused blood to the arterial side of a patient in need of supplementary, extracorporeal blood circulation. The other channels, at least two, comprise the remainder of the available volume (i.e., about 10%–50%) with each channel integrated into the wall of the large central passageway. Generally, the available volume is determined by calculating the area of a cross-section of each longitudinal passageway and multiplying by the length. Since the length is about the same in each case, the relative volume for each channel will be directly proportional to the cross-sectional area of each passageway.

More specifically and with reference to FIG. 12A, the multichannel catheter has distal and proximal ends that correspond approximately to the distal and proximal ends of the shaft 134 of the obturator as shown in FIG. 12A. The long distal portion 130 of the shaft of the obturator of FIG. 12A fits into the large lumen for the flow of blood and has a blunt or rounded end 136. The obturator has a handle 138, allowing the physician or assistant assisting in the operation to have control of the obturator. A cross section of the obturator J—J is shown in FIG. 12B. The obturator has two channels 140, that corresponds to the other two channels of the catheter, as discussed hereinafter. The large central, first channel, (i.e., a passageway or lumen) of the multichannel catheter of this invention, is defined by a surrounding wall that extends substantially the length of the catheter, is closed at its distal end, and has at least one outflow opening for extracorporeal blow flow along the length of the catheter, as discussed in greater detail hereinafter. The catheter has at least second and third channels, each of which extends substantially the length of the catheter, parallel to said first channel but independent thereof. Together, these additional channels (2, 3 or more) comprise not more than about fifty percent of the available internal channel volume of the catheter and are preferably integrated into the wall of the first channel. In a three-channel configuration, the second channel (generally the larger of the two smaller channels) is open at its distal end, while the third channel's distal end is in communication with the interior of an inflatable bladder, i.e., a balloon. The catheter further preferably has a plurality of openings in the wall of the first channel extending part of the length of the first channel, some near the distal end of said catheter communicating only with the first channel. These openings are ports or outlets for blood from a cardiopulmonary machine. The balloon is integrated into the distal end of the catheter between the first channel blood outflow openings and second channel's distal opening. The blood flow openings are said to be "upstream" or proximal of the balloon, while the distal opening of the second channel is said to be "downstream" or distal of the balloon. The interior of the inflatable means communicates with the distal end of the third channel through an opening in the wall of the catheter.

As discussed, the catheter can be a disposable, flexible polymeric (e.g. polyurethane) tube with at least three lumens with an inflatable balloon, e.g. polyurethane at the distal end of the cannula. The catheter is combined with the obturator so that the shaft of the obturator is snugly situated inside the first channel and slidably positioned along the length of the first channel. The outside diameter of the cannula is suitable for insertion into a femoral artery. The catheter's central lumen or channel is for the delivery of arterial blood through multiple distal outlets all upstream (relative to blood flow from a cardiopulmonary machine) of the distal balloon, a lumen that communicates with the aorta in the area of the aortic root for delivery of cardioplegic solution (and left ventricular venting, if desired), and a small lumen for control of the distal balloon. Radio-opaque balloon indicator and insertion depth marks aid in positioning the device into a patient. The catheter is preferably a non-pryogenic, single use, sterile device, which is packaged individually.

This device is intended for use in arterial perfusion of the aorta, via a femoral artery, in cardiovascular surgery procedures requiring extracorporeal cardiopulmonary bypass (CPB) with required blood flow rates of one to five Liters per Minute. Generally, the Maximum Recommended Blood Flow Rate is five Liters per Minute.

Figure 6A:
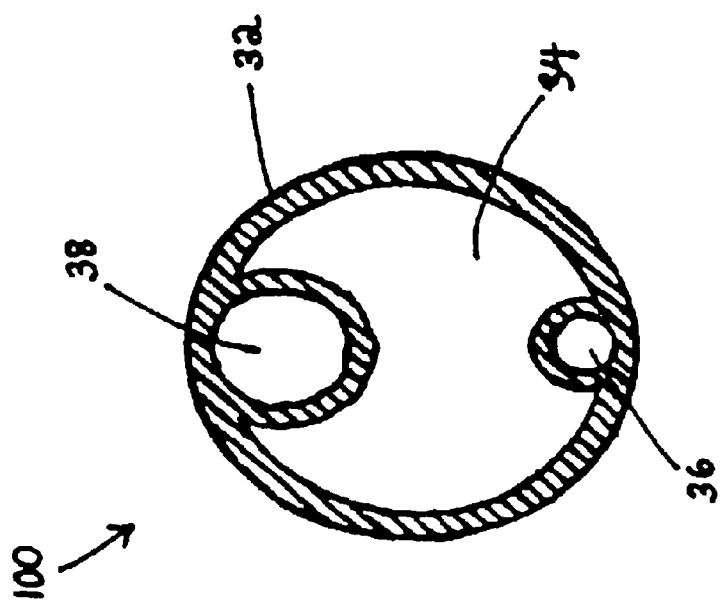

Turning now to FIG. 4, one can see a detailed representation of the catheter of this invention which is a cross-sectional view of the length of the catheter without an obturator in the blood flow lumen. A cross section of the catheter 100 is shown generally as having a proximal end 31 and a distal end 33. The large central first channel 34 is defined by the wall 32 of the catheter. The second channel 36 and the third channel 38 are shown as being integrated into the wall of the first large channel. The second and third channels are integrated with the wall 32 of the first channel 34 and are shown as having an interior wall portion 41 defining the smaller second and third channels. This can be seen more clearly in FIGS. 6A and 6B. In FIGS. 6A and 6B one can see a cross section of the catheter 100 having a large central lumen 34 and smaller lumens 36 and 38 that are integrated into the wall 32. A blood outflow portal 40 is shown in part in FIG. 6B.

Figure 8:
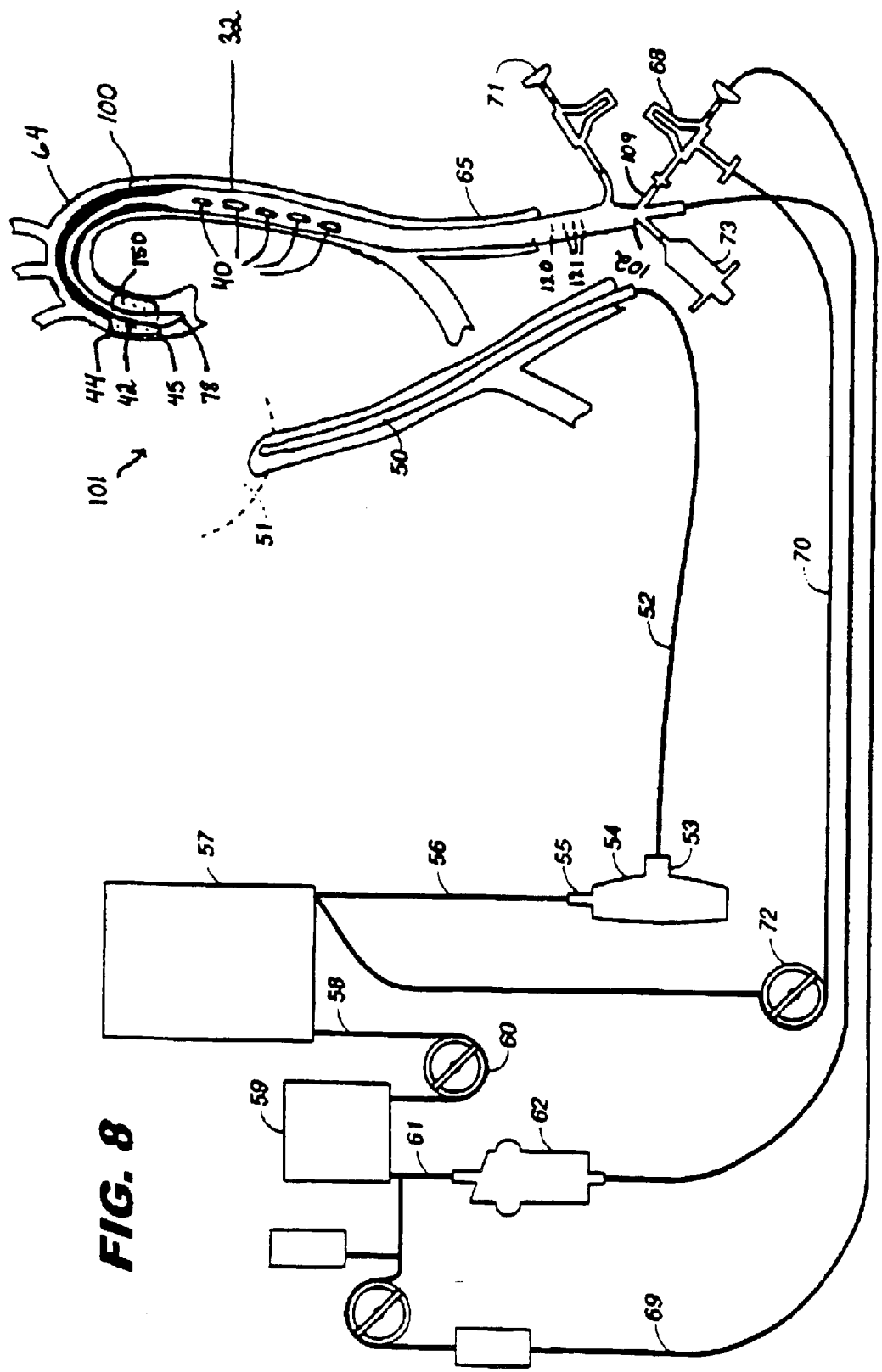
FIG. 8 shows a cardiopulmonary system using the catheter of this invention.
Figure 9:
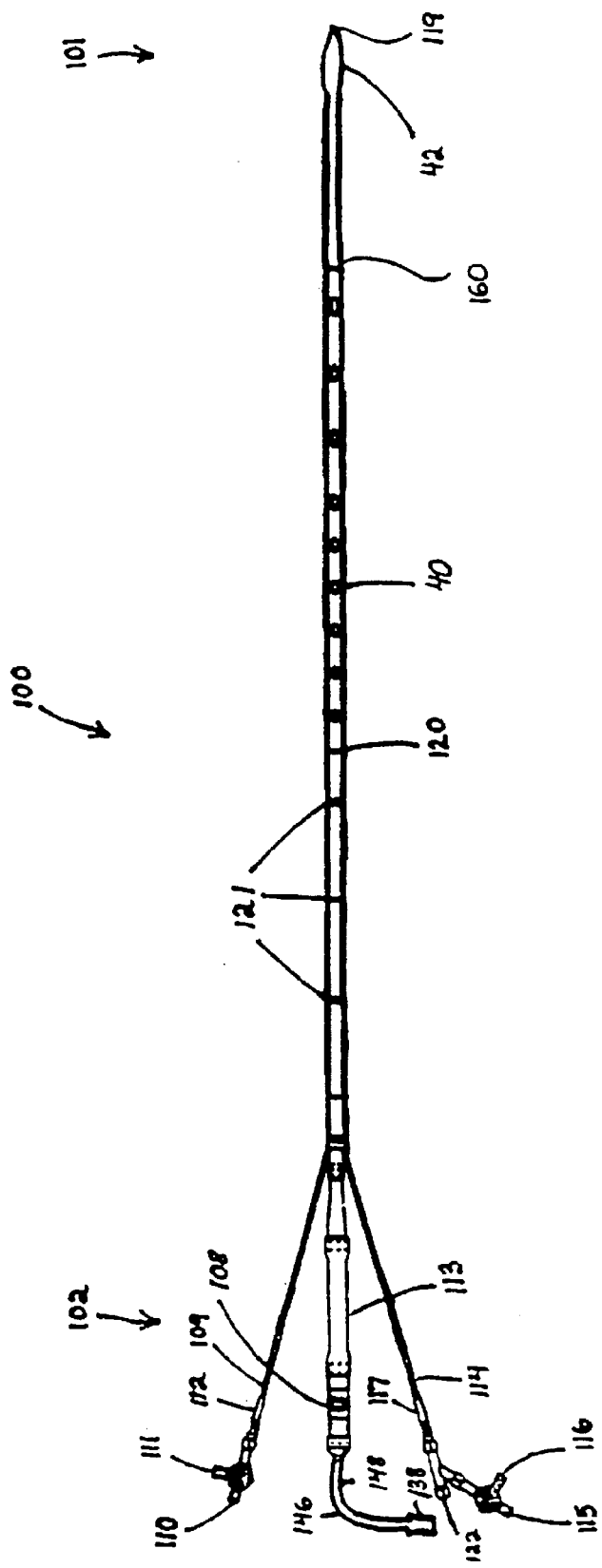
FIG. 9 is a representation of a preferred aspect of the balloon catheter of the invention having an internal obturation.
Figures 10A, 10B:
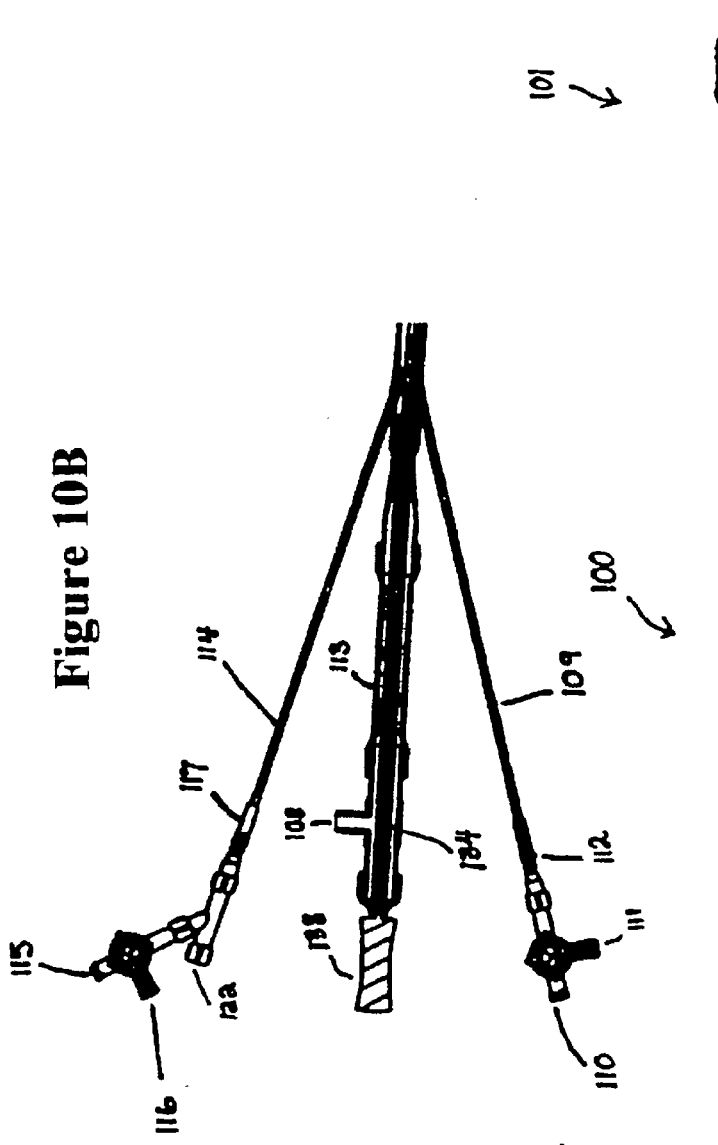
FIG. 10A shows a preferred aspect of the balloon catheter of the invention having an internal obturation.
FIG. 10B shows a magnified view of a portion of 10A.
Figure 13:
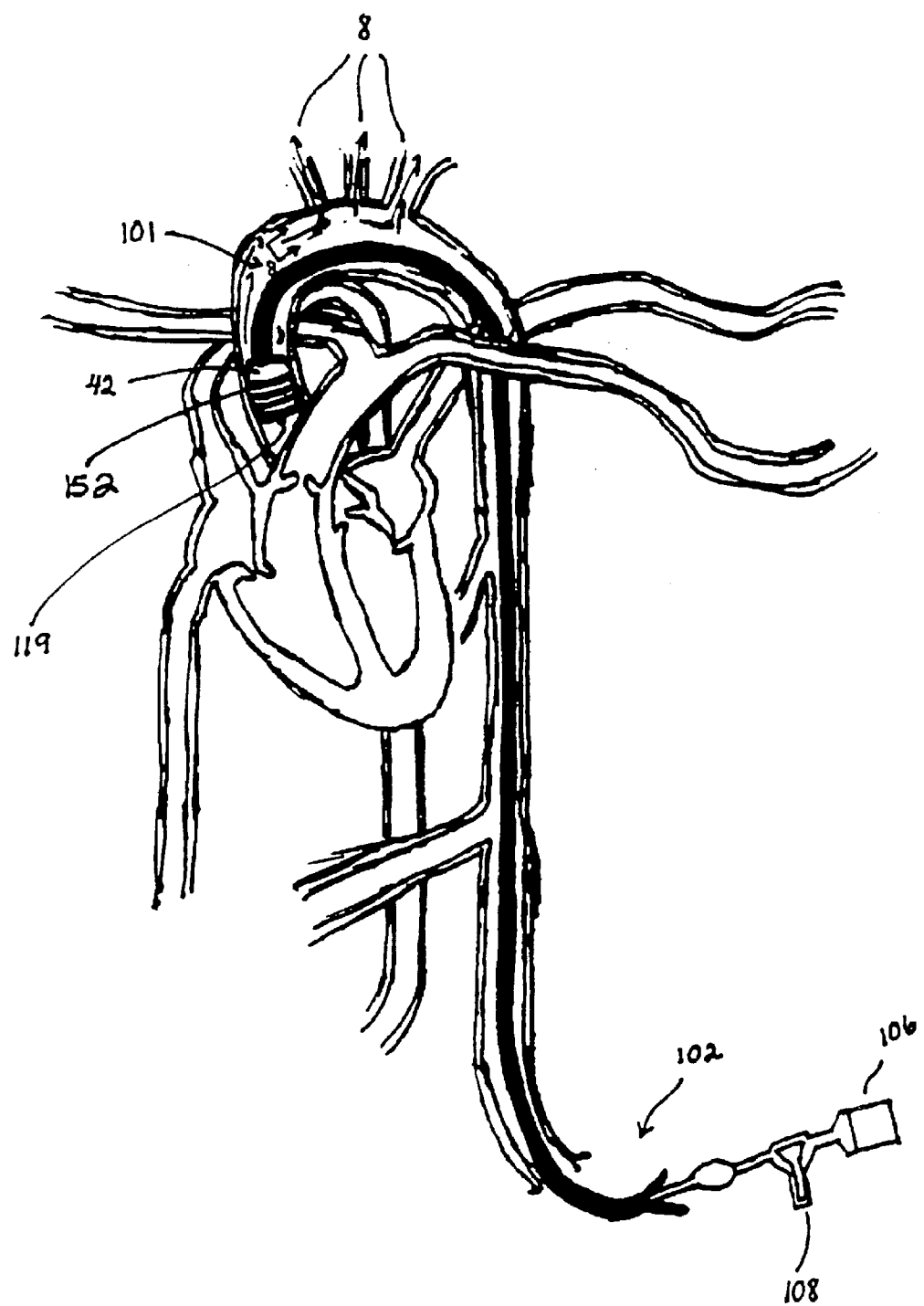
FIG. 13 is a schematic representation of how the catheter of the invention works in a mammal's heart and circulatory system.
Figure 15:
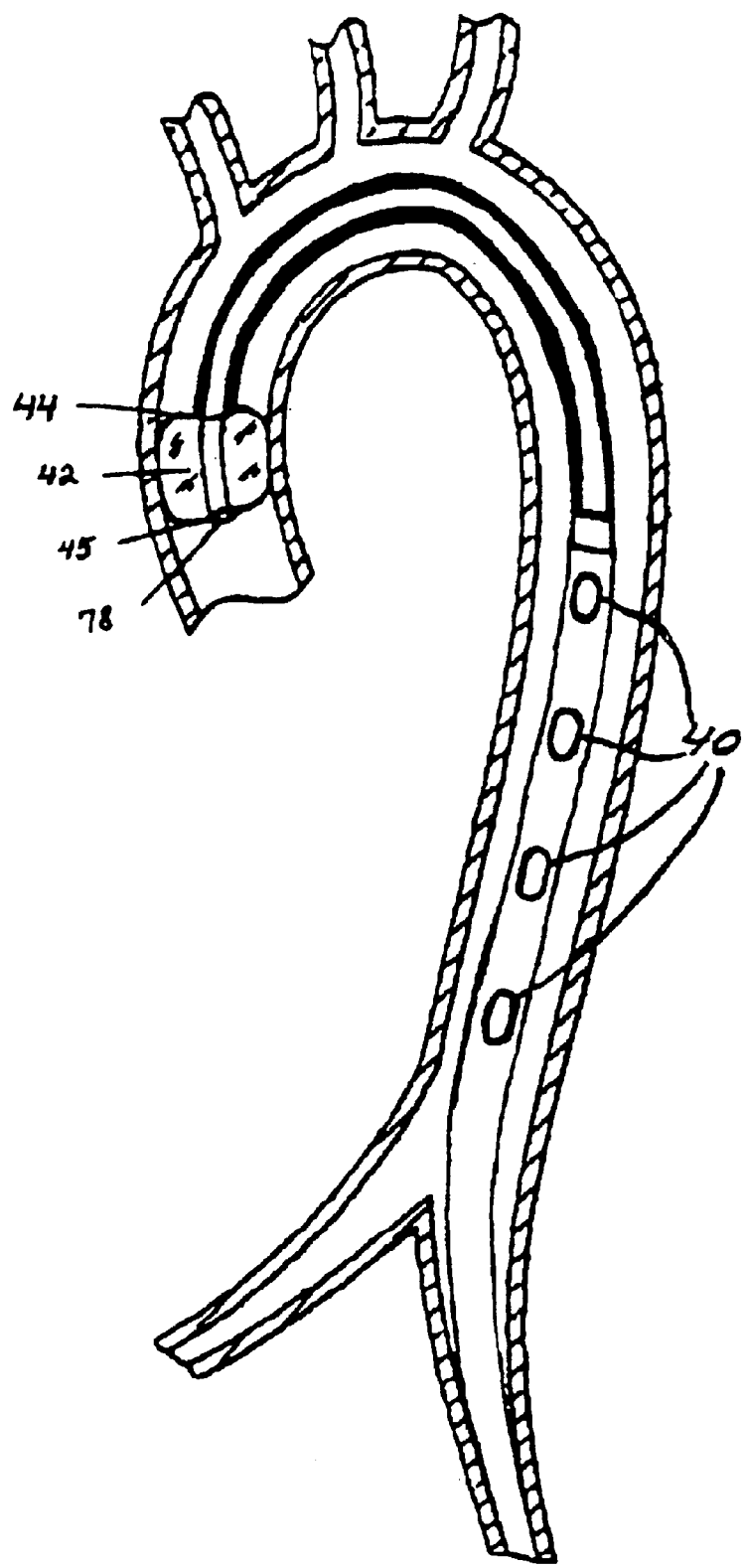
FIG. 15 shows the balloon catheter of this invention properly positioned within the ascending aorta.

In FIG. 4, toward the distal end 33 of the catheter 100 are located openings 40 that are outlet ports for the fluid passing through the channel 34. In use, that fluid will be extracorporeal blood that is circulated to the arterial side of a patient in need of such extracorporeal circulation. As will be discussed in greater detail, hereinafter, the catheter of this invention is preferably designed to be inserted into a femoral artery of a human patient and advanced sufficiently so that the distal end is positioned in the ascending aorta. Thus, the catheter, and preferably the obturator, must be flexible enough to readily bend at its distal end as shown in FIGS. 13 and 15. The catheter, and preferably the obturator are designed to minimize kinking to avoid reduced fluid flow through the passageways 34, 36 and 38 as shown in FIG. 4. The openings 40 as shown in FIG. 15, are located on the proximal side (i.e. upstream) of the inflatable bladder 42. The openings 40 may be spread along the length of catheter as shown in FIGS. 8, 9 and 10A. Blood from the cardiopulmonary machine will flow in the direction of the arrow as shown in FIG. 4 and out the blood outlet ports 40 along the length of the catheter with some flowing out of channel 34 near the great arteries. As shown in FIG. 4, while some of the openings may be adjacent the balloon 42, for example within about an inch of the proximal edge 44 of balloon 42, the openings 40 are located such that they do not contribute to kinking of the catheter as it passes the aortic arch. Thus the openings 40 are located in the distal portion of the catheter so that when the catheter is positioned as shown in FIG. 8 the openings are in a region of the catheter that is relatively straight. A few of the openings may be located immediately adjacent the proximal side of the balloon 42 (e.g., within about an inch of the proximal edge 44 of the balloon 42), while the majority will be along the distal 50% of the catheter.

Figure 16:
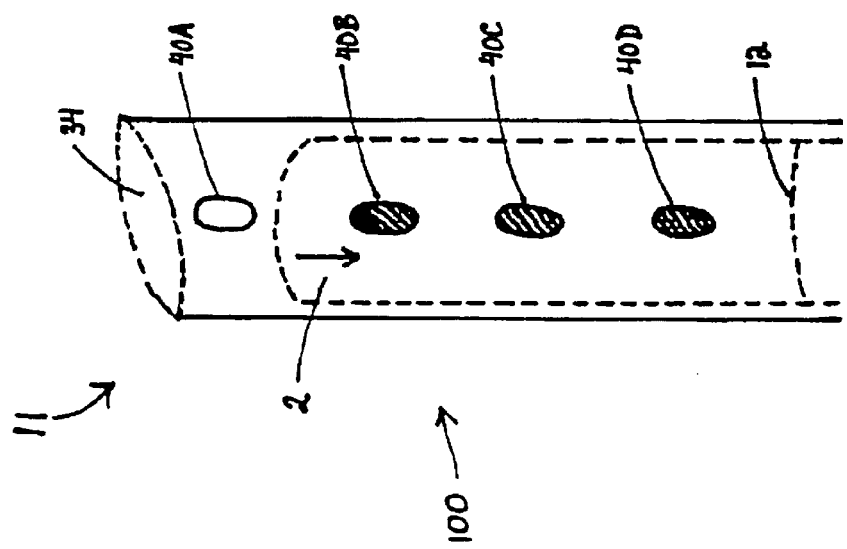
FIG. 16 shows an alternative view of a catheter that is inserted through the ascending aorta.

FIG. 16 shows a perspective view of a portion of blood delivery catheter 100 in combination with the obturator 2. The view of FIG. 16 is a perspective view with the obturator shown inside the channel 34 and is shown by dotted lines as the outline of the obturator. The blood delivery catheter is shown as having blood outlet ports shown as 40A–40D for blood to come out along the length of the catheter. Blockage of the ports is shown by the wavy lines 142. This is shown in simplest form and will be explained in that manner. In operation, if one wishes to deliver blood to an artery, one would enter the femoral artery, e.g. through a percutaneous opening, or cut down, and insert the distal end of the blood flow catheter/obturator combination. Once the catheter is inserted into the artery, it is moved up the artery to be positioned as desired so that the balloon is at the ascending aorta. One can see that if the obturator is not present on the inside of the blood flow catheter (from FIGS. 4, 9 or 10A), blood flowing in the artery would flow into cavity 34 and through a port nearest the distal tip out through other ports 40. On the other hand, if the obturator is snugly positioned in the interior of the catheter in channel 34 and positioned as shown, and the distal tip 101 of the blood delivery catheter is inserted into the artery, blood will enter the lumen 34 through port 40A, but will not exit ports 40B–40D that are more proximal because the internal flow of the blood from the heart and artery would be blocked by the obturator. As the catheter is inserted further and further along into the femoral artery, the obturator can be withdrawn in the opposite direction of the arrow shown in FIG. 4. Once all ports 40 are positioned so that they are inside the artery, the obturator can be withdrawn to a point designated as 12 in FIG. 16, without having to worry about blood entering lumen 34 exiting outside of the body. Thus, the obturator is withdrawn as the catheter is inserted until it reaches a point where blood from a cardiopulmonary machine can be added to the internal blood flow lumen at its proximal end as will be discussed in more detail hereinafter.

It is important that the total outflow capacity of the outlet ports 40, 40A–40D (as shown in for example, FIGS. 4, 10A, 15, and 16) is greater than the inflow capacity of the blood flowing into the catheter. This will mean that total collective cross-sectional area of openings 40 will exceed the total cross-sectional area of channel 34. Thus, to calculate the collective cross-sectional area of openings 40, one determines the area of each opening and adds the area of each opening. Preferably the total area (i.e. outflow capacity) of the openings will exceed the cross-sectional area (i.e. inflow capacity) of channel 34 by at least a factor of 1.2. Having a factor of greater than about 2 is even more preferable. For example, if the radius of channel 34 is 2.5 mm, the cross-sectional area is 19.6 (2.5×2.5×3.14=19.6) and the total cross-sectional area of the openings 40 will be at least 23.6 (1.2×19.6=23.6), more preferably 39.2 (2×19.6=39.2). Preferably, each opening has a cross-sectional area of about 3–40 mm$^2$, preferably about 5 to about 20 mm$^2$. The total number of openings may be as few as three large openings up to about 20 or more openings of various shapes.

While the shape of the openings 40 may be of any appropriate shape for the outflow of blood, it is preferable that some, generally a majority of the openings are elongate in shape. While the openings may be positioned in any configuration toward the distal end of the catheter, for example, the longitudinal axis of the elongate openings may be positioned substantially parallel to the length of the catheter or at a slight angle such that it forms a helical design or the length could be perpendicular to the length of the catheter. However, it is preferred that the elongate openings have the length of the opening substantially parallel to the length of the catheter. While at least one opening 40 in the wall will be present, the number of openings that can be present may vary from 2 to 20 or more but must be placed in a manner that the structural integrity of the catheter is maintained. By having elongate openings instead of circular openings the sheer stress on the blood is reduced by allowing the blood to flow out of the outlets more easily. In addition to the elongate openings located in the distal region of the catheter as shown in FIG. 4, other openings may be located further upstream of the elongate openings 40. Further designs may be seen in FIGS. 8, 9 and 10A. The design of the openings 40 may generally be that of an oval, a rectangle, a trapezoid or some similar elongated design. In general, they will be approximately one cm to about four cm, e.g. about 2.5 cm long with a width at the broadest portion of the opening no more than about 5 mm. The openings 40 are positioned toward the distal end of the largest channel so that when the catheter is positioned with the balloon 42 in the ascending aorta, the openings are near the great arteries so that blood can flow more freely to the great arteries to ensure the necessary oxygenation of tissues (i.e. perfusion) for the rest of the body. The outlet ports may be spread along about the distal 60% of the largest channel. By having a majority of (e.g., oval) openings and ensuring the outflow capacity exceeds the inflow capacity, the sheer stress on the blood passing through the first channel 34 will be significantly reduced. By having elongate openings at the distal end and maximizing the size of channel 34, the flow rate through the large channel 34 may be up to six liters (L) per minute without having adverse affect on the blood due to too much shear stress on the red cells, platelets or white cells. Having elongate openings and proper outflow capacity, reduces the pressure drop between the proximal end where the catheter is attached to the cardiopulmonary machine and the exit at the openings 40. Generally, the pressure drop will be under 300 millimeters of mercury and preferably under 200 millimeters of mercury. The pressure drop can be further reduced by having additional holes towards the proximal end of the catheter but preferably somewhere between the midpoint of the catheter and the distal end. This design is seen in FIG. 10A. As discussed before, the openings 40 will be positioned and constructed to minimize the chance of kinking when the catheter passes over the curve of the aortic arch and generally will be sufficiently proximal of the balloon 42 with the largest cross-section of openings to be positioned in a section of the catheter that remains straight. While, a few (e.g., 2–4) small openings may be placed within about 2.5 cm proximal of the balloon 42, the majority are about 7.5 cm to about 30 cm on the proximal side (i.e., upstream) of the balloon, depending on the catheter sizing for the patient.

In general, the maximum length of the multichannel catheter of this invention will be that length necessary to insert the catheter into the femoral artery of the patient and moving it up the artery to place the distal end having the balloon within the ascending aorta. Depending on the size of the patient, whether a child or an adult, the length may be from about 40 centimeters up to about 120 centimeters or more. Generally, the range will be about sixty to about one hundred centimeters with about eighty-five centimeters being an average length suitable for most people. The length will be significantly less when used in open-chest surgery with aortic insertion or brachiocephalic cannulation. The length of the associated obturator will be in the same range, but will be somewhat shorter in that the distal tip of the obturator will not necessarily have to extend to the distal tip of the catheter.

Turning to FIG. 12A, one sees the length 144 of the obturator 146 which can be used in the combination of the invention. Generally, the length 144 of the obturator 146 will be sufficiently long so that it will be inserted into a multichannel catheter which will be positioned so that a balloon at the distal end of the catheter will block the ascending aorta between the brachiocephalic artery and the coronary ostia. While the obturator 146 may fit the entire length of the multichannel catheter to the end of the blood flow channel and thus may extend over the aortic arch, it will generally be sufficient to only extend to the second opening from the distal end of the multichannel catheter. The length of the obturator's distal end 130 will generally be from about 40 cm up to about 120 cm. The exact length of the obturator will depend on the size of the patient that is being operated upon, whether a child or an adult. Generally, the length of the obturator will be about 60 to about 100 centimeters with about 85 centimeters being an average length suitable for most people. The handle portion 138 of the obturator will be of a size that is large enough for the physician or assistant assisting in the operation to push the obturator in or pull it out. Generally, the length of the handle will be anywhere from about 3 to 15 centimeters. The obturator and the handle 138 may be extruded from one polymeric material or the handle may be bonded to the distal portion of the obturator through heat bonding or using an appropriate adhesive such as Dymax 19 IM. The material that can be used for the obturator is any material that is bio-compatible with a patient's blood, that is, it is physiologically acceptable and will not have an adverse affect on the patient when used in the manner it is intended. The bio-compatible material for preparing the obturator will have to be of the nature that it will readily slide into and out of the lumen that is carrying the blood. Depending on what material the multichannel catheter lumen has in its lining, the preferred material will be a pulomeric substance that has a significant degree of flexibility. On the other hand, it will be not be so flexible that it is unable to easily be moved throughout the channel. A material that is particularly useful is low density polyethylene or hytrel. Other polymeric material that can be used includes polyvinylchloride (PVC) which has been plasticized using a plasticizer such as trioctyl trimellitate (TOTM) or di (2-ethyl-hexyl) phthalate (DEHP). Suitable PVC resin is available from Dow Chemical Corporation, Midland, Mich., or the Polomer Technology Group (PTG) Inc., Emeryville, Calif. Other polymers that are useful include medical grade polyurethane, polysiloxane containing co-polymers which may be also referred to as surface modified additions (SMAs). These polymers may be blended with a base polymer before processing or coated on a blood contacting surface. When blended with the base polymer, the SMA will migrate to the polymer surface resulting in a high concentration of the SMA on that surface which has fewer adverse effects with the blood that contacts it. Other polymers may be apparent to those of ordinary skill upon further consideration of this invention.

It is advantageous to design the catheter so that the distal portion of the catheter that transcends the aortic arch has only the two smaller channels. Thus, the distal end of large channel 34 would not go around the aortic arch. This means that the distal portion would have less lumen volume and more polymeric material volume, thus reducing the likelihood that the distal end would kink and possibly block the flow of fluids through one of the channels 34, 36 or 38. Thus, another aspect of the invention is the catheter, wherein the distal portion that transcends (and bends around) the aortic arch, has fewer channels than the rest of the catheter. In this case, the obturator would only extend to the distal end of the blood flow channel and not to the inflatable bladder. In this case, the obturator would be significantly less than the full length of the catheter.

The outside diameter of the multichannel catheter of this invention will be such that it can be inserted and moved through the femoral artery of the patient and located in the ascending aorta as discussed above. Generally, this will have an outside diameter (OD) of no more than about 30 French, preferably of about 18 to 24 French with about 20 to 22 French outside diameter fitting most patients. The French scale is a scale used for denoting the size of catheters or other tubular instruments, with each unit being roughly equivalent to 0.33 millimeters (mm) in diameter. For example, 18 French indicates a diameter of about 6 millimeters while 20 French would indicate a diameter of about 6.6 millimeters. The thickness of the wall 32 may be between about 0.2 mm to about 1.0 mm. Thus, the inside diameter of channel 34 will generally not exceed about 28.2 French, and may vary from about 14.8–22.5 French.

The obturator 146 of this invention as shown in FIG. 12A, has a solid, flexible shaft 134 to slidably engage the blood-flow channel to block the flow of blood. The shaft 134 has a distal portion 130 for inserting into the channel and a proximal portion 148 that comprises a handle 138 for pushing the distal portion 130 into the lumen to be blocked or pulling the distal portion out of the lumen. Generally, the distal portion 148 has a cross-section that is less than the cross-section of the handle 138 and will have a cross-sectional dimension, which, at its widest part, is of a size that is no larger than the inside dimension of the blood delivery tube that is inserted into an artery such as a femoral artery, for delivery blood to a mammal particularly a human. Thus, the cross-sectional dimension will be no more than about 28.2 French (i.e. about 9.4 mm) and may vary from about 14.8–22.5 French. It is preferably no more than about 21 French (about 7.0 mm), and more preferably less than about 18 French (about 6.0 mm). The cross-sectional configuration will be one that conforms to the cross-sectional configuration of the lumen that the obturator shaft is blocking. It may have a circular, square, trapezoidal, or other design, but generally will be circular with adjustments made for the internal shape of the lumen. Examples can be seen in FIGS. 5A–5E, 6A–6B and 12B. FIG. 12B is a cross-section of the obturator of FIG. 12A along lines J—J. Here the cross-section is circular with portions 140 of the circle removed to accommodate certain channels in the lumen into which the shaft is inserted. This is better depicted in FIG. 10B, which shows the shaft 134 of FIG. 12A in place in a multi-lumen catheter.

In some cases, it may be useful to provide the multichannel catheter of this invention with a distal end that has a slight "preshaped" region designed into it. The preshaped region is designed to correlate to the aortic arch. In inserting the catheter the preshaped region is maintained in a relatively straight condition by using a stylet, i.e., a stiff plastic support mechanism positioned in channel 34. This can be used in conjunction with a guide wire positioned in channel 36. When the distal end of the catheter reaches the curve of the aortic arch, the catheter continues to be advanced via the femoral artery, but the stylet is slowly withdrawn allowing the precurved region to bend around the aortic arch to have the balloon then located past the brachiocephalic artery but before the coronary ostia.

In other cases it may be useful not to have a preshaped distal region but instead have a straight end that is of a durometer rating that allows it to transcend the aortic arch by following the arch, making a "U" turn of essentially 180°, allowing the balloon to be properly positioned for inflation in a stable position. This may be achieved by bonding a distal portion that has only the two smaller lumens 36 and 38, thus making the distal portion less susceptible to kinking, as discussed above.

As shown in the FIG. 10A, at the distal end 101 of the catheter of this invention there is located a inflatable bladder 42 which in general is a balloon that is attached to the distal end of the catheter. The interior of the inflatable bladder is in fluid communication with the third channel 38 so that the balloon can be inflated or deflated by transporting fluid through the channel to the balloon to inflate it, or sucking the fluid out to deflate the balloon. The design of the balloon may be any design known in the art, such as that shown in U.S. Pat. Nos. 5,423,745; 5,516,336; 5,487,730; and 5,411,479, the pertinent parts of which are incorporated by reference. Useful balloon components are commercially available to one of ordinary skill. While one balloon is shown in FIGS. 9, 10A and 16, multiple balloons could be used, e.g., two. However, for ease of use and preparation, one balloon is preferred. It is also preferred that the distance between the proximal edge 44 of the balloon and the distal side 45 as shown in FIG. 16 be such that the surface contact of the wall of the balloon with the interior wall of the ascending aorta wall be maximized. This helps ensure a tight seal to prevent leakage. This distance between 44 and 45 may be from about 20 mm to about 50 mm, preferably about 30 mm to about 40 mm.

Turning now to FIG. 10B, one sees a closeup of the distal end 102 of the catheter of the invention. It should be understood that the figures are representative, and are not necessarily drawn to scale. This is an external view that shows the elongate openings 40 and a balloon 42 in its inflated form, although not fully inflated. In general, the balloon is preferably of an oblong shape (i.e., its longitudinal cross-section appears to be cylindrical) as shown in FIGS. 8 and 16. This maximizes the surface contact with the ascending aorta wall and minimizes the stress on the vessel wall by dispersing the pressure over a greater area. By maximizing the surface contact, the position is maintained to a greater extent.

The forces imposed upon the wall of the ascending aorta are evenly distributed over the surface area contacted using a cylindrical balloon such as that disclosed in the multi-channel aortic balloon catheter of the invention, and shown in FIG. 15. A spherical balloon, such as Heartport's catheter model EARC-23EAC, known in the art, concentrates and directs all of the force towards a smaller area of aortic wall near the apex of it's curvature. While the magnitude of the concentrated force from a spherical balloon is equivalent to that of a cylindrical balloon, a distributed force resulting from a cylindrical balloon poses less problems in terms of balloon stability. This is due to the fact that the cylindrical balloons tend to naturally orient the forces perpendicular to the aortic wall more so than a balloon which is spherical in shape by distributing the force over a larger surface area.

Applicant's cylindrical balloon as shown in FIG. 15 cannot "pivot" within the ascending aorta as easily as a spherical balloon due to the increased surface contact with the wall of the ascending aorta and has, therefore, an increased propensity for stability.

The design of the distal portion of the multichannel catheter of the invention that transcends the aortic arch is such that the radial forces exerted by the tip of the catheter are less influenced by curvature or angulation of the shaft of the catheter. That is, there is a change (reduction) of structural rigidity of the catheter from the end of the blood flow lumen 34 to the distal end of the device. This facilitates positioning of the catheter tip. The balloon located on or around the catheter can be used to position (or control position) the catheter in the desired orientation within the ascending aorta. This "desired" position can be a central or eccentric location. The shape, size, materials, mounting and physical characteristics of the balloon can be modified as so to control the desired positioning of the catheter within the blood vessel.

Forces that influence the balloon stability include those of the balloon against the aortic wall, those of the wall against the balloon, and those exerted by the catheter shaft (e.g. leverage and torsion). These forces will continue to search for a point of balance until it is found. Until balance is obtained the balloon will remain unstable within the ascending aorta.

Asymmetrically mounted balloons, such as Heartport's, known in the art, provide greater opportunity for instability due to their inability to effectively balance the opposing forces between the balloon and the wall of the ascending aorta.

Applicant's preferred balloon as shown in FIG. 16 is designed to be symmetrically mounted, providing the best opportunity to balance and equalize the opposing forces between the balloon and the wall of the ascending aorta.

Balloon taper should be minimized in order to maintain cylindrical profiles as shown in FIG. 15. Tapered balloons may orient the catheter tip towards the outside of the aortic arch. As the balloon is then inflated the inflation axis of the balloon (perpendicular to the catheter shaft) is not oriented perpendicular to the walls of the aortic arch, its orientation becomes increasingly parallel to the walls of the aortic arch. This then allows the balloon to continue it's expansion parallel to the aortic arch which in turn forces the catheter tip into the wall of the ascending aorta possibly resulting in occlusion of the cardioplegia lumen.

To prevent occlusion of the cardioplegia lumen and/or damage to the inside wall of the aorta, the physician or assistant can monitor the progress of the ascending multi-channel catheter of the invention into the aorta. Transesophageal Echocardiography (TEE) monitoring or Fluoroscopic Monitoring are useful to monitor balloon occlusion function.

While the surface of the balloon may be smooth, as shown in FIG. 15, it preferably has a design on it that provides additional friction between the balloon surface and the internal surface of the aortic arch. Thus the balloon surface may have either depressions 150, as shown in FIG. 8, or ridges 152, as shown in FIG. 13 in a design that helps maintain the balloon's position. It is preferable to have on the surface of the balloon certain ridges or bumps indicated in FIG. 13 as 152 to provide additional friction for maintaining the position of the balloon in place and minimizing the disruption of plaque that may be present. Generally, the volume of the balloon will be about 30 to about 100 cubic centimeters, preferably about 30–60 cc. The length of the balloon from its proximal end 44 to its distal end 45 will generally be about 2.5 cm to about 7.5 cm with about 4 cm being particularly satisfactory. It will need to expand sufficiently to block the ascending aorta completely so that blood does not get to the arrested heart from the cardiopulmonary machine.

Turning again to FIG. 4, the second channel 36 is designed to introduce a cardioplegia solution, to evacuate fluid (i.e., vent the left ventricle), or to carry a guidewire or various types of probes for treating the heart. Thus, it has at least one opening 37 at the distal end 33 of catheter 100 downstream of balloon 42. This allows a cardioplegia solution or the appropriate fiberoptic cable to be inserted into the channel and moved through the channel out exit 37. It also allows for a negative pressure to be applied to vent the left ventricle of the heart.

In a preferred mode of operation, the catheter of this invention is inserted percutaneously or by cutdown into the femoral artery of a patient and is threaded through the femoral artery to the ascending aorta to be positioned there. It may be necessary to supplement the flow of a patient's heart if it has been weakened, and this can be done by flowing oxygenated blood through the central passageway 34 out the outlets 40 to the great arteries and other arteries in the arterial system. If an operation is to be performed on the heart, which requires arrest of the heart, the catheter is positioned appropriately, the balloon is inflated to block the flow of blood into the heart from outflow openings 40. Cardioplegia solution is administered through channel 36 out opening 37 to arrest the heart and blood is circulated through channel 34 out openings 40 to maintain circulation of oxygenated blood in the patient during the operation.

Turning now to FIGS. 5A through 5E and FIG. 6A–6B, one can see a cross-sectional view taken along lines 5—S in FIG. 4. In these figures, it can be seen that the large central passageway 34 is defined by the wall 32 of the overall catheter and that the channels 36 and 38 are integrated into the wall 32. They may be integrated so that they are positioned more interiorly as shown in FIG. 5A or more exteriorly as shown in FIG. 5B with cross-sectional diameters that are essentially a circle. On the other hand, in FIG. 5C, the cross-sectional of channels 36 and 38 may be elongated, oval, or of a "bow-tie" configuration. Other examples of possible configurations of channels 36 and 38 are shown in FIGS. 5D and 5E. While the relative volumes of the two are shown to be about equal, the total volume of flow available for all passageways 34,36 and 38 is divided as follows. The amount of fluid flowing through passageway 34 will be at least about fifty percent or more (e.g., up to about 90%) in order to achieve the advantages of this invention with the flow through passageways 36 and 38 being the remaining fifty percent or less (i.e., down to about 10%). In general, there will need to be less volume in the channel for communicating with the balloon than in the channel that is available for the cardioplegia or the fiberoptic instruments or cable. While generally, it is preferable to have the channels 36 and 38 opposed one hundred eighty degrees from each other as shown, for example, in FIGS. 5A to 5C and 6B, it may be possible to have them adjacent as shown in FIG. 5E. Having them adjacent makes the preparation a bit more difficult than having them opposed as in FIGS. 6A–6B.

The ratio of the total volume of the cardioplegia channel 36 to the balloon inflating channel 38 will vary from about 1:1 to about 4:1. So, for a multichannel catheter in which about 70% of the total available volume is provided for the channel 34 and about 30% of the total available volume is provided for channels 36 and 38, channel 36 will account for about 15% to about 24% with channel 38 accounting for about 15% to about 6%. Alternatively if channels 36 and 38 collectively account for about 10% of the total available volume then channel 36 will have about 5% to about 8% while channel 38 will have about 5% to about 2%.

By referring to FIG. 7, one can see the relative proportions of the three channels of the multi-channel catheter of this invention. In the Figure the abbreviations have the following meanings:
ID—inner diameter
OD—outside diameter
IWT—inner wall thickness
OWT—outer wall thickness
Summarizing the dimensions, they are as follows:
OD 32: 16–30 French (5.3–9.9 mm)
ID 32: 14.8–28.2 French (4.7–9.3 mm)
OWT 32: 0.6–1.0 French (0.2–0.3 mm)
IWT 41: 0.6–1.0 French (0.2–0.3 mm)
ID 38: 0.6–1.0 French (0.20.3 mm)
ID 36: 0.64.0 French (0.2–1.3 mm)

The catheter of this invention is able to handle a blood flow rate through the central channel 34 of about one-half up to about 6 liters per minute with the proper sizing and design. Generally, a flow of about five liters per minute is sufficient to handle the vast majority of circulatory needs required by patients having heart surgery performed. On the other hand, the flow of cardioplegia solution or drug-containing solution through channel 36 is generally about 100 to about 300 cubic centimeters (0.1–0.3 liters) per minute. The balloon inflation channel 38, which is generally smaller than channel 36, will be of a size sufficient to carry balloon-inflating fluid, e.g., saline, to the balloon. The volume of the balloon is generally about 40 cc to about 100 cc, generally about 60 cc. Thus, channel 38 is of a size sufficient to carry that volume over a short period of time, i.e., less than a minute and generally less than about 10 seconds. The volume of the balloon will be greater if the distal end of the multichannel catheter is tapered in the region covered by the balloon.

In general, the catheter of this invention will need to be flexible enough to easily be inserted up through the femoral artery to be positioned in the ascending aorta. The flexibility needs to be sufficient so that the catheter can bend but will not kink at body temperature. In general, this flexibility is measured by Durometer and will be in the 50 to 80 range. Generally, we will have a Durometer reading of about 60. It is preferable that the distal end where the balloon is located is somewhat stiffer than the rest of the catheter. This helps to ensure the positioning of the balloon in the ascending aorta to ensure that it does not get displaced during the operation.

In performing open heart or less invasive cardiac surgery, generally, it is necessary to do an angiogram by placing an angiogram catheter up the femoral artery and positioning it in the ascending aorta. Based on the length of the angiogram catheter, balloon placement position can be determined, the multichannel catheter of this invention has markings indicating its length measured from the distal end to various distances near the proximal end so that the physician knows exactly how far to insert the catheter of this invention. Having that information indicated on the catheter makes it easier for the physician to do the insertion and also reduces the need to use fluoroscopy to properly insert the catheter. On the other hand, if a angiogram catheter measurement is not done before inserting the catheter of this invention, an ultrasound probe may be used to position the catheter of this invention where the catheter of this invention carries a detectable beam on the tip of the catheter. Alternative methods may be employed for positioning the catheter, such as guidance by fluoroscopy or echocardiography, fiberoptic visualization through the catheter, magnetic or electronic guidance, or other means of insuring proper placement.

The material which is used to manufacture the multichannel catheter of this invention may be any material that is physiologically acceptable, that is it is made of a material that will not have an adverse effect on the patient when used in the manner in which it is intended. Generally this will require the use of biocompatible material (i.e. the body will not react with it) for preparing the catheter of this invention. In addition, the material that is used must possess sufficient stability and flexibility to permit its use in accordance with the process of the invention. Various biocompatible polymers may be used. A polymer that is particularly valuable for preparing the catheter of this invention is polyvinyl chloride (PVC) blood tubing, that has been plasticized. Preferably, the plasticizer which is used in the PVC is trioctyl trimellitate (TOTM), while the standard plasticizer is di-(2-ethylhexyl) phthalate (DEHP). TOTM plasticizer is less extractable than DEHP and produces a better blood response. Suitable PVC resin is available from Dow Chemical Corp., Midland, Mich., or Polymer Technology Group (P.T.G.) Inc., Emeryville, Calif. Another polymer that is useful for preparing the multichannel catheter of this invention is medical grade polyurethane. Other polymers may be prepared based on a family of polysiloxane-containing copolymers termed surface modified additions (SMAs). These copolymers may be blended with the base polymer before processing or coated on the blood contacting surface. When blended with the base polymer the SMA will migrate to the polymer surface resulting in a high concentration of the SMA of that surface, which has fewer adverse reactions with the blood that contacts it. When coated, device surfaces are pure SMA. High surface concentrations of the SMA are responsible for the improved biocompatibility of extracorporeal circuit components. Plasticized PVC is particularly useful as the base polymer. A further description of these polymers is given in article entitled "Surface Modifying Additives for Improved Device-Blood Compatibility" from ASAR Journal 1994 M619–M624 by Chi-Chun Tsai et al., The article is incorporated herein by reference. Such polymers are available from P.T.G. Corp.

Other useful polymers include polyurethane-urea biomaterials that are segmented polyurethane (SPU) some of which have surface-modifying end groups (SMES) covalently bonded to the base polymer. These are described by Ward, et al. in an article entitled "Development of a New Family of Polyurethaneurea Biomaterials" in Proceedings From the Eighth Cimtec—Forum on New Materials Topical Symposium VIII, Materials in Clinical Applications, Florence, Italy, July, 1994. See also U.S. patent application Ser. No. 08/221,666, which is incorporated herein by reference.

Sometime the blood interacts with artificial surfaces of polymers in such a way that the blood coagulates on the surface creating thrombi. These thrombi can block the catheter or blood vessels, preventing the blood from flowing and causing oxygen depletion and nutrient starvation of the tissues. Thus, the surface of the polymeric material used for the multichannel catheter of this invention should not give rise to thrombus formation. An anti-thrombotic agent can be used to prevent the clots from forming. Some of the blood polymer interactions are discussed in article entitled "Biomaterials in Cardiopulmonary Bypass" found in Perfusion 1994; 9: 3–10 by James M. Courtney et al.

Polymer modifications that permit an improvement in blood compatibility while maintaining acceptable levels of other fundamental properties include the treatment of surfaces with protein, the attachment of anti-thrombotic agents and the preparation of biomembrane-mimetic surfaces. The preferred anti-thrombotic agent is the anti-coagulant heparin which can be attached ionically or covalently. Preferably it is attached covalently.

An additional factor to consider in preparing the catheter of this invention is the relative roughness of the blood-contacting surface. Excess surface roughness has deleterious effects on blood flow through the catheter and should be avoided.

Another article that discusses the factors relating to compatibility of surfaces contacting blood is entitled "State-of-the-Art Approaches for Blood Compatibility" from Proceedings of the American Academy of Cardiovascular Perfusion Vol. 13, Jan. 1992, pages 130–132 by Marc E. Voorhees, et al.

Turning now to FIGS. 9, 10A, 10B and 11 one can see an overall view of the catheter of this invention. The catheter is generally shown as 100 having a distal end 101 and a proximal end 102. At the distal end one sees the inflatable bladder, or balloon, 42. Along the length of the catheter are a series of ports or openings 40, which allow blood to flow through the large inner channel, as discussed hereinbefore. The obturator or flexible shaft is shown in part as 146, with an enlarged handle portion 138 and a reduced distal portion 148 that slidingly engages the internal channel, not shown, to block the backflow of blood once the catheter is inserted into a femoral artery. The obturator 146 (in FIG. 12A) is shown in FIG. 9 as being partially withdrawn from the internal channel. An enlargement of the obturator end inserted into the internal channel is shown in FIG. 10A as encompassed in the area defined by a dotted line. The openings 40 are darkened to indicate that the obturator is positioned to block all of the outlet ports. Once the obturator is inserted into a patient's femoral artery the tip of the obturator is drawn through the blood flow channel until it is located proximal of the inlet port 108 for blood from a cardiopulmonary machine. The cardiopulmonary machine is connected so that the oxygenated blood enters the port 108 and then flows through the inner channel through the catheter and out through the ports 40 to then circulate to the arteries of the patient. At the distal end of the catheter, the channel for, i.a., the cardioplegia solution is attached to a cardioplegia line 114 which in turn leads to a port 115 for the import of cardioplegia fluid which can be pumped through line 114 and the inner channel out through the cardioplegia outlet port 119 at the distal end of the catheter. A port 116 is available for monitoring the cardioplegia/aortic root pressure to determine if any adjustments need to be made to the flow of the cardioplegia. A label 117 can be placed on the line 114 to ensure that the doctor knows which line is for the cardioplegia A hemostatic valve 122 is shown through which a guide wire can be threaded as discussed hereinafter. At the proximal end 102 of the catheter 100 there is a connection for a line 109 for the balloon inflation fluid to enter the channel that leads through the interior of the catheter to the balloon at the distal end 101 of the catheter 100. Attached to the balloon inflation fluid line is a port 110 for connecting to the syringe containing the balloon inflation fluid. Also located at the proximal end of the catheter is a port 111 for monitoring the balloon inflation pressure to insure that enough pressure is provided to the balloon. A label 112 will label the line for the balloon inflation fluid. The distal end of the obturator is shown at 160 by means of a solid line, even though the obturator is inside the catheter. In FIG. 9 the obturator is partially withdrawn. As the obturator is withdrawn further and further eventually the end of the obturator will be drawn to a point where it is proximal to, i.e. to the left of, the inlet port 108 for the blood. The oxygenated blood from the cardiopulmonary machine will then enter the port 108 and flow through the inner blood flow channel and out through the ports 40. The last flow of the blood can be adjusted by clamping the flexible connecting hose 113 with a suitable pinch clamp. This can affect the flow of blood through the catheter.

Figure 11:
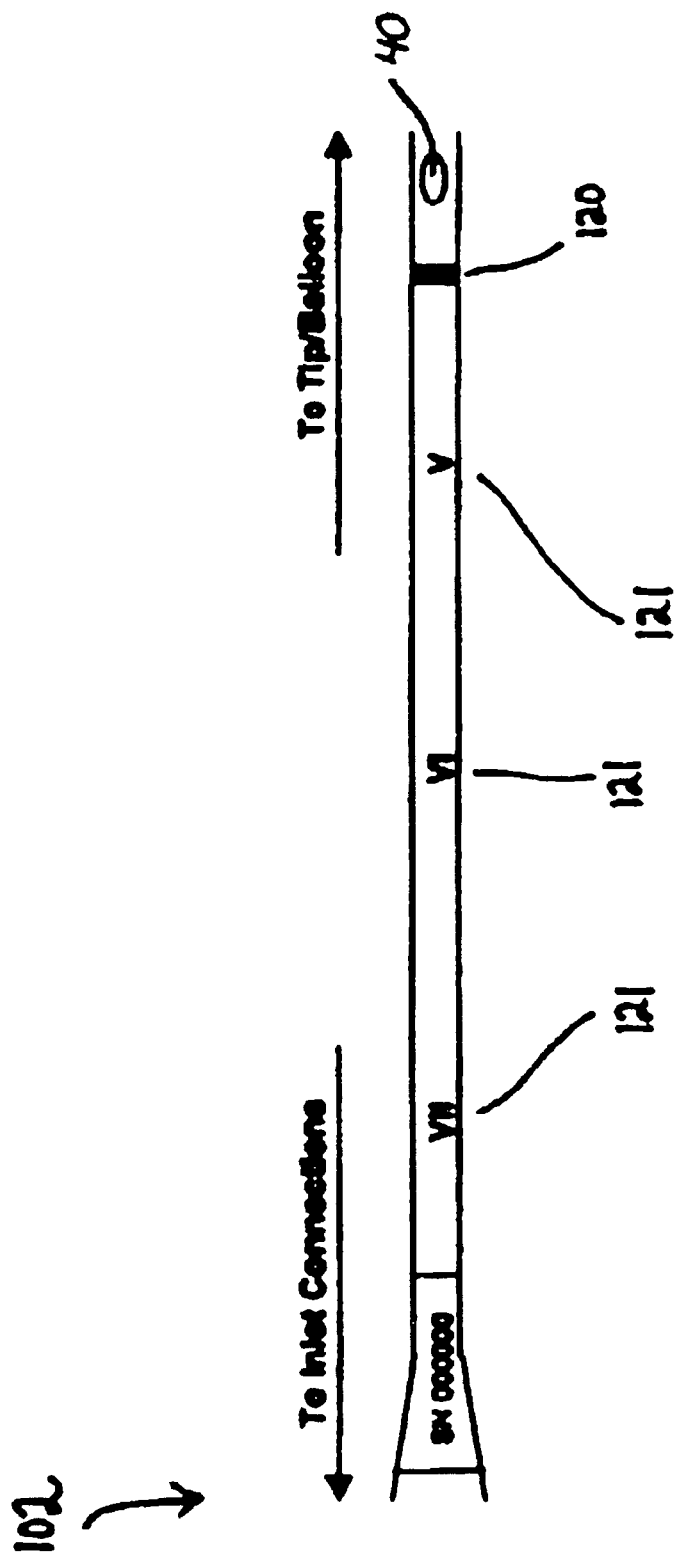
FIG. 11 shows a partial view of the balloon catheter of the invention having positioning indicators located along the central passageway of the device.

FIGS. 10A and 10B show a similar view of the catheter of this invention. The necessary attachments for the cardioplegia, blood flow, and the balloon inflation fluid. The numerals in 10A and 10B are similar to those used in FIG. 9. In FIG. 11, a close-up of a portion of the proximal end 102 of the catheter is shown where the positioning indicators 121 are marked. At the right hand side of the FIG. 11, a warning indicator 120 is located which would be for example, 25 mm from the first outlet port 40 shown in the figure. This is useful as one is withdrawing the catheter from a patient as a warning that an outlet port would be appearing soon and that the obturator should therefore be positioned back in the blood flow channel to prevent the backflow of blood once the heart has resumed its beating and pumping of blood. The other positioning indicators 121 shown as V, VI and VII show the number of centimeters, e.g. fifty, sixty, or seventy respectively, from the distal tip VII of the catheter. These are useful to help the surgeon position the catheter prior to surgery when the exact distance to the ascending aorta has been determined. The serial number SN000000 is shown to identify the device that is being used.

Turning now to FIG. 13, one sees the catheter of this invention positioned with the balloon 42 located and expanded in the ascending aorta. The catheter is shown as being shaded in the proximal portion 102 to represent the obturator (being inserted) into the catheter to the point where the distal portion transcends the aortic arch. Thus the portion transcending the aortic arch has only 2 channels: one that leads to outlet 199 and one that leads to the interior of the balloon 42. The handle 106 of obturator can be used to withdraw the obturator from the blood flow channel to a point where the obturator is no longer blocking port 108. A cardiopulmonary machine can be attached to port 108 to allow oxygenated blood to flow into the catheter and our the blood flow ports 40, not shown in the drawing.

Figure 14A:
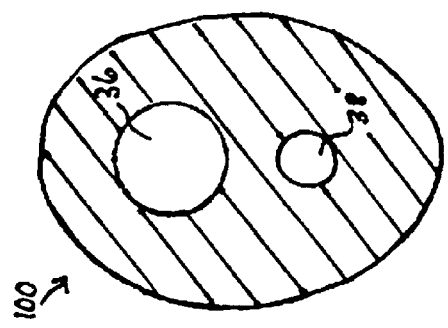
FIGS. 14A, 14B and 14C show cross-sectional views of the distal portion of the balloon catheter of this invention.
Figure 14B:
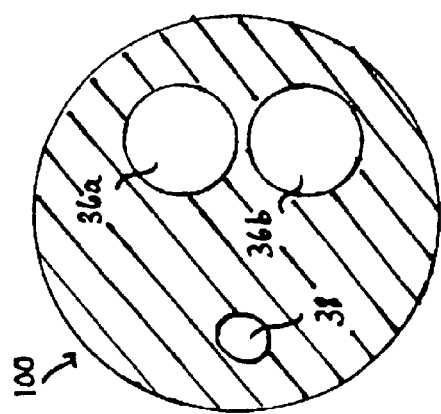
Figure 14C:
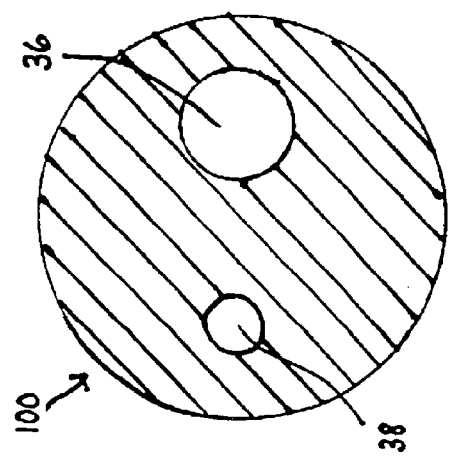

Turning now to FIGS. 14A, 14B, and 14C, one can see a cross-sectional view of the distal portion of the catheter of FIG. 13. FIGS. 14A and 14C depict two-channel arrangements, while 14B depicts a three channel arrangement. In these figures, the numerals have the same designation as those in FIGS. 5A–5E. Thus 36 designates the cardioplegia or venting channel and 38 designates the balloon-fluid channel. The shaded portion represents polymeric material.

Uses of the Catheter of This Invention

The catheter of this invention may be used in several different ways. For a condition in a patient that needs supplementary extracorporeal blood circulation because of insufficient circulation from his or her own heart, the catheter may be introduced via a femoral artery, positioned as appropriate and attached to a cardiopulmonary bypass machine to circulate blood through the large central channel 34 and out openings 40. When appropriately positioned with the distal end of the catheter in the ascending aorta, a fine fiber optic cable may be threaded through second channel 36 to examine the aortic area of the heart. If it is determined that a heart operation is necessary, the balloon may be inflated through channel 38 to block the ascending aorta, cardioplegia solution may be administered through channel 36 to arrest the heart, and oxygenated blood from a cardiopulmonary machine is pumped through channel 34 and openings 40 into the arterial pathway of the patient's circulatory system. Thus, the device of this invention may be used in cardiovascular surgery in general or various heart examinations or treatments of artery and valvular disease. Cardiovascular surgery is meant to include surgery to the heart or to the vascular system of a patient. The catheter is particularly useful in cardiac surgery, whether open chest surgery or minimally invasive heart surgery. Such surgery may include, but are not limited to, the following:

1. Coronary artery revascularization such as:
   (a) transluminated balloon angioplasty, intracoronary stenting or treatment with atherectomy by mechanical means or laser into the coronary arteries via one lumen of the catheter or
   (b) surgical mobilization of one or both of the mammary arteries with revascularization achieved by distal anastomoses of the internal mammary arteries to coronary arteries via a small thoracotomy.
2. Any atrial or ventricular septal defect repair such as by
   (a) "closed" cardioscopic closure or
   (b) closure as in "open" procedure via a thoracotomy or other limited access incision.
3. Sinus venosus defect repair similar to above.
4. Infundibular stenosis relief by cardioscopic techniques.
5. Pulmonary valvular stenosis relief by cardioscopic techniques.
6. Mitral valve surgery via thoracotomy.
7. Aortic stenosis relief by the introduction of instrumentation via a lumen in the aortic catheter into the aortic root.
8. Left ventricular aneurysm repair via a small left anterior thoracotomy.

One unique aspect of the multichannel catheter of this invention is its ability to be adapted to be used in accordance with the needs of a patient. For example, a patient with symptomatic coronary artery disease undergoes a diagnostic evaluation to determine the type of treatment that best suits that patient's condition. As a result of the evaluation, the physician may recommend surgical treatment, interventional cardiology treatment or some alternative treatment. Interventional treatment may include percutaneous transluminal coronary angioplasty, atherectomy or the use of a stent to keep the vessels open. Alternative treatment may include the use of a laser or myoplasty.

If additional treatment is recommended, the multichannel catheter of this invention is particularly valuable in the further evaluation to determine the condition of the patient, the type of treatment recommended and the type of drugs that might be useful to administer to the patient. Thus, in using the multichannel catheter of this invention, the catheter is inserted into a femoral artery by percutaneous puncture or direct cut-dow. The distal end of the catheter, which carries the balloon, is inserted first and moved through the femoral artery to be positioned in the ascending aorta, as discussed in more detail hereinafter. Initially, the physician performing the work may wish to introduce instruments through the channel 36 in FIG. 4 or other probes to allow observation or measurement of the internal condition of the artery, aortic arch and/or aortic semilunar valve. A cardioscope, an electrophysiology probe, a transmyocardial revascularization probe, a radiation probe, or the like may also be inserted through channel 36. Once observations are made concerning the condition of the heart and associated arteries, the physician can then take additional steps. For example, it may be desirable to administer a biologically active fluid directly to the heart or aorta using an appropriate liquid composition containing an active entity appropriate for the patient's condition. The active entities in such a biologically active fluid include drugs (particularly those having cardiovascular effect) that are pharmaceutically acceptable small organic molecules, small polypeptide molecules, larger polypeptide molecules, and even a DNA or RNA that may be useful for gene therapy. Examples of useful molecules include those useful as antianginals (e.g., organic nitrates, calcium channel blockers, beta-adrenergic antagonists) antihypertensive, antiarrhythmics, antihyperlipoproteinemias, myocardial contractile enhancers, anti-atherosclerotic agents, and the like. Such fluids especially for cardioplegia can best be delivered through channel 36 in FIG. 4, but alternatively can be delivered in the fluid used to inflate balloon 42 through channel 38 in FIG. 4. In the latter case, the material used for the balloon would be semipermeable to allow the drug to diffuse through the balloon membrane. A drug having lipid-dissolving characteristics can be delivered through the balloon membrane. Alternatively, it may be useful to deliver such an active agent by adding it to the cardiopulmonary machine reservoir.

Once the catheter is in place, and observations regarding the internal conditions have been made, the physician and/or assistant can then move on to the next steps. For example, less invasive surgery, as discussed in U.S. Pat. No. 5,452,733, may be performed on a beating heart with no initial cardiopulmonary support, i.e., no blood would flow through the catheter and heart would continue to function. If at any time, the physician would decide that cardiopulmonary support would be needed, supplemental blood flow from a cardiopulmonary (heart/lung) machine could be started and work could be continued with a beating heart or a fibrillating heart. Once a decision is made to completely arrest the heart, cardioplegia solution is delivered to the heart through the channel 36 after balloon 42 is inflated to block the flow of blood to the heart from the cardiopulmonary machine. As described, the multichannel catheter of the invention can be used in least invasive surgical procedures as well as open chest surgery.

The multichannel catheter of this invention is particularly useful in performing heart surgery where the heart is arrested using a cardioplegic solution and blood is circulated to the patient via a cardiopulmonary bypass machine. In this case oxygenated blood is circulated through the large channel of the catheter of this invention. The introduction of negative pressure on the venous drainage system may be used to enhance venous drainage and reduce the need to vent the right side of the heart. Generally, the negative pressure may be maintained at the vena cavae regions (superior and inferior) using a centrifugal pump attached to a standard femoral venous cannula. A system for performing such a process is depicted in FIG. 8.

In general, the process for preparing for cardiovascular surgery or for performing surgery on a patient's heart comprises a sequence of steps, which from the standpoint of using the catheter of this invention, includes three steps that are performed sequentially: (a) once a cut-down or percutaneous opening is made in the patient to access e.g. the femoral artery, the distal end of the catheter described herein is inserted into the femoral artery (the flexible shaft or obturator is slidingly engaged in the blood flow channel to prevent backflow of blood); (b) the catheter is positioned so that the inflatable balloon is positioned in the ascending aorta; and (c) the obturator is removed, i.e. withdrawn sufficiently, to allow the blood flow channel to be connected to a cardiopulmonary machine to pump blood into the channel at its proximal end. Prior to, during, or after insertion of the catheter into the femoral artery, a single femoral access cannula is inserted into the patient's femoral vein to position it so the distal open end of the cannula is adjacent the vena cava region of the patient's heart and the proximal end of the cannula is attached to a cardiopulmonary bypass machine through a centrifugal pump wherein the cardiopulmonary bypass machine comprises a blood oxygenation means fluidly connected to the centrifugal pump.

The multichannel catheter is positioned within the subject's blood circulatory system such that the distal end of said catheter is positioned in the ascending aorta such that the first channel openings are located along the distal length of the catheter (as discussed before), the inflatable means is located on the cephalid side of the aortic valve and the distal end of the second channel is located proximate the aortic valve and downstream of the inflatable means.

About the time a source of oxygenated blood from the cardiopulmonary machine is connected to the proximal end of said first channel of the catheter, a source of cardioplegia fluid is connected to the proximal end of said second channel. A source of fluid is connected for inflating the balloon to the proximal end of said third channel and the balloon is inflated to block the flow of blood to the heart Cardioplegia solution is pumped into the heart to arrest the patient's heart. With the obturator withdrawn, oxygen-rich blood is pumped through said first channel out the first channel openings upstream of the balloon at rate sufficient to maintain the subject's metabolism and perfusion while at the same time oxygen-depleted blood is removed from the patient's vena cavae regions through the femoral vein cannula by applying a negative pressure using the centrifugal pump. The physician can then perform a surgical operation on the heart as needed and the patient is maintained as needed.

Referring to FIG. 8, the femoral vein is accessed percutaneously or by cut down using the appropriate size standard femoral access cannula 50 (such as an Research Medical Inc. #TF-030-050). This cannula conducts de-oxygenated venous blood from the vena cava 51 to PVC tubing 52 (e.g. 0.5 inch inner diameter). This tubing is attached to the negative pressure (inlet) port 53 of a centrifugal pumping device 54 (such as the St. Jude Medical #2100CP); the positive pressure (outlet) port 55 of the centrifugal pumping device is connected via tubing 56 (0.5 inch ID PVC) to a venous reservoir system 57 (such as the COBE Cardiovascular, Inc. VRB 1800). This configuration pulls blood from the vena cava 51 to the venous reservoir 57. Utilization of negative pressure in this manner to provide venous blood return eliminates the need to "vent" or empty the right heart. By using a centrifugal pump that reaches about −20 to about −50 millimeters of mercury (mm Hg), a sufficient negative pressure is maintained. The use of a closed reservoir system is preferred to eliminate air/blood interface and associated blood trauma. The venous blood exits the reservoir through tube 58 (e.g. ⅜ inch ID PVC tubing). This tube is connected to an oxygenator/heat exchanger means 59 (such as the COBE Cardiovascular, Inc. model #CML DUO #050-257-000) to oxygenate the oxygen-depleted blood. The blood will be pumped through the membrane/heat exchanger by a roller pump device 60 (such as the COBE Cardiovascular, Inc. model #043-600-000). The oxygenator will oxygenate the blood and the heat exchanger will regulate blood temperature. The oxygenated arterial blood will exit means 59 through tube 61 (such as ⅜ inch ID tubing), pass through an arterial filter 62 (such as a COBE Cardiovascular, Inc. Sentry #020-954-000) and be delivered into the femoral artery via the multichannel catheter 100 of this invention. Preferably, all blood contact components are surface modified to reduce blood trauma and patient inflammatory response and to meet requirements for anticoagulation of patient's blood.

The multichannel cathether 100 of this invention provides a flow of oxygenated blood to the aorta 64. The invention catheter 100 is introduced into the femoral artery 65 percutaneously or by cut-down. The invention catheter 100 may be introduced utilizing a guidewire and stylet. The stylet provides stability to the catheter allowing the device to resist kinking during insertion with a minimum required wall thickness of the catheter. Accurate positioning of the balloon will differ from other positioning methods by utilizing measurement of the catheter. The appropriate distance will be determined and indicated on the femoral artery catheter 100 prior to insertion; the positioning indicators 121 and warning indicator 120 will provide simple and accurate balloon positioning. Accurate positioning of the balloon tip may also be enhanced or verified using visualization by transesophogial echo or fluoroscopy.

The invention catheter provides a flow of oxygenated blood to the aorta as part of the cardiopulmonary bypass process. The catheter is of a length sufficient to extend from the insertion point in the femoral artery to the ascending aorta as shown in FIG. 8, which length will vary depending on the size of the patient, as discussed hereinbefore. The catheter has a proximal end 102 and a distal end 101. The catheter has an inflatable balloon 42 located on the proximal side of the distal tip for fixing the catheter within the ascending aorta. The channel extending the length of the catheter to the balloon has a port at the proximal end of the catheter that communicates with the balloon so that the balloon can be filled with a fluid from a syringe-type inflation device 73 to occlude the ascending aorta as discussed herein. The catheter also has (a) a channel extending from the proximal end 102 to outlet ports 40 upstream of the balloon for delivering oxygenated blood and (b) a channel extending through the entire cannula with an outlet port 78 in the distal tip for a guidewire and/or delivering a cardioplegia solution to the heart through stopcock 68 into inlet line 109 at the end of line 69. Changing the position of the valve in stopcock 68 to connect with line 70 and providing a negative pressure by roller pump 72, allows for the venting of the left ventricle by pulling fluid from the left ventricle through the semilunar valve through opening 78. Optionally, a line is available for optical fibers to be inserted at port 71.

Another aspect of this invention may be viewed as an improvement in the process of minimally or "least" invasive heart surgery. For traditional open heart surgery, the surgeon is required to make a long incision in the front of the chest and divide the sternum bone to gain access for the procedure. In minimally invasive heart surgery, a series 47 of small incisions are made and the operation is carried out through narrow tubes or ports, using direct or video assisted visualization. Such a minimally invasive process and associated techniques are described in various aspects in U.S. Pat. Nos. 5,433,700; 5,458,574; and 5,452,733, all of which are incorporated by reference in their entirety.

How to Make the Catheter

Generally the multichannel catheter of this invention is prepared using any technique that provides the multichannel catheter herein described. The key is to ensure that the second and third channels are integrated into the wall of the first channel. This may be done by forming the channels separately then conjoining them, i.e. by gluing or other means. However, the multichannel catheter may be made through a mandrel-dipping technique, or preferably a continuous extrusion process. Extrusion involves forcing a fluid polymer material (as discussed above) through a suitably-shaped die to produce the cross-sectional shape, such as that depicted in FIGS. 5A through 5E and 6, or other suitable shape as described herein. The extruding force may be exerted by any standard means known in the art such as by a piston or ram or by a rotating screw, which operates within a cylinder in which the polymeric material such as PVC or polyurethane is heated and fluidized. The fluid material is then extruded through the die in a continuous flow. The extrusion head will have a multitubular die to provide a continuous multichannel catheter, essentially as described herein. Using a mandrel-dipping technique, a mandrel having the desired size and cross section design is dipped in or drawn through a fluid polymeric material so that the mandrel is coated with the polymer. The polymer is then dried on the mandrel and removed to give the desired design. This technique may be done at commercial manufacturers, e.g., PTG, Emeryville, Calif. or Extrusioneering, Temucula, Calif., and others.

Once the multichannel catheter is formed, whether by extrusion or mandrel-dipping, it is cut to suitable lengths and treated to provide the further characteristics of the product to make it operable. Such treatment may occur in any particular order. For example, a plurality of openings 40 in FIG. 4 are formed near the distal end of said catheter communicating with said first channel. These openings are made in conformance with the designs discussed herein, and thus are preferably elongate in that the longitudinal axis of the elongate design may be helical or orthogonal, but is preferably substantially parallel to the longitudinal axis of the catheter itself. The openings may be provided by suitably cutting or punching the elongate design into the wall of the catheter. The design is approximately oval, rectangular, or the like with the length of the opening being about a size discussed herein before. The width of the opening will be such it will not weaken the structural integrity of the distal end of the catheter. FIGS. 8, 9 and 10 present various configurations for the positioning of openings 40. Optionally, additional openings communicating with the first channel may be provided along the length of the catheter positioned between approximately the middle of the catheter and the elongate openings near the distal end. The openings are useful in reducing the pressure drop between the proximal end of the catheter and the distal openings to help reduce the sheer stress on the blood.

In addition to the openings that communicate with the first, large channel, at least one opening communicates with the third channel. An inflatable bladder, i.e. a balloon device, is integrated into the distal end of the catheter such that the interior of the balloon communicates with the outlet of the third channel to allow fluid to flow through the third channel and to the interior of the inflatable means. In general, this may be integrated by positioning a balloon having an opening corresponding to the opening to the third channel and adhering the balloon to the distal end of the catheter between the openings to the first large channel of the catheter and the distal tip of the catheter. This adherence may be performed by using a suitable glue, solvent bond, light sensitive weld, or other suitable material known in the art for this purpose. The material used for the inflatable means may be any suitable biocompatible material that is capable of being inflated and deflated a plurality of times. Polyurethane-based biocompatible polymers are preferred. These are described in the aforementioned article by Ward, et al.

Finally, the distal end of the first, large channel and the third, small channel are closed. This may be achieved by plugging, solvent sealing, heating or other suitable means. The process must be carried out in such a way that the distal end of the second channel remains open.

Alternatively, a catheter of this invention may be constructed by conjoining, e.g. a 3 or 4 channel portion (which has the large blood flood channel) with a portion that has one less channel, i.e. the distal portion in FIG. 13.

In this case, the catheter is produced by introducing, e.g. 3 or 4 single lumen extruded tubings into a molded manifold which merges each of the single lumens (3) into the mulitluwnen extrusion. See FIGS. 5A–5D. The multilumen extrusion of the proximal portion is fused or bonded to the distal multilumens extrusion using mandrels which prevent closure of the continuing lumens, e.g. 36, 36a, 38 in FIGS. 5A–5D. The balloon is fused or bonded onto the distal portion of the tubing with fewer lumens, which portion is designed to transcend the aortic arch.

The proximal portion of the multichannel catheter of this invention is prepared using any technique that provides the multichannel catheter herein described. Once the proximal portion of the multichannel catheter is formed, whether by extrusion or mandrel-dipping, it is cut to suitable lengths and treated to provide the further characteristics of the product to make it operable.

The distal portion of the catheter is similarly extruded to give a length having a cross-section show in FIGS. 14A, 14B, or 14C. The openings of the distal portion (e.g. 36 and 38 of 14A) that correspond to openings of the proximal portion (e.g. 36 and 38 of FIG. 5A) are aligned, mandrels are positioned to prevent a closure of the communicating lumens, and the distal and proximal portions are fused or bonded or otherwise permanently conjoined.

The inflatable bladder is integrated into the distal end of the catheter such that the interior of the balloon communicates with the outlet of the balloon communicating channel to allow fluid to flow through the lumen channel and to the interior of the inflatable means. In general, this may be integrated by positioning a balloon having an opening corresponding to the opening to the appropriate channel and adhering the balloon to the distal end of the catheter. As noted before this adherence may be performed by using a suitable glue, solvent bond, light sensitive weld, or other suitable means known in the art for this purpose. The material used for the inflatable means may be any suitable biocompatible material that is capable of being inflated and deflated a plurality of times. Polyurethane-based biocompatible polymers are preferred. These are described in the aforementioned article by Ward, et al.

Preparing A Patient for Cardiovascular Surgery Using A Catheter of the Invention This is a representative process for using the catheter of this invention, given as a step-wise approach.

1. Preoperative screening of patients includes evaluation by sufficient methods (such as clinical examination, segmental doppler examination, aortogram) to exclude those with aortoiliac disease or anatomy that would preclude safe introduction of the catheter of this invention into the aorta from a femoral artery.
2. The patient is anesthetized, positioned, prepped and draped for cardiovascular surgery requiring, e.g. cardiopulmonary bypass. Arterial pressure is monitored using a right and left brachial or radial artery pressure monitoring line, which should be continuously simultaneously monitored, sudden differences in right and left pressure may indicate balloon blockage of innominate artery. Intraoperative monitoring with transesophageal echocardiography (TEE) is required. Fluoroscopy with capability of imaging the thoracic aorta may be used but is not an alternative to intraoperative monitoring with (TEE). The aortic arch and ascending aorta should be evaluated for the presence of atherosclerotic disease associated with luminal projections, a contraindication for use of the catheter of this invention. The aortic valve should be inspected for significant insufficiency, a contraindication for delivery of cardioplegia in the aortic root with the catheter of this invention.
3. The catheter of the invention is removed from its package using sterile techniques. The integrity of the occlusion balloon is checked by placing the distal end (balloon-tip) of the catheter into a basin of sterile saline solution while inflating the balloon with 20 cubin centimeters (cc) of air. If air bubbles are visualized leaking from balloon or balloon bond area the catheter is to be replaced. Air should then be removed by gentle aspiration, completely collapsing the balloon against the main body of the catheter. A 20 cc syringe filled with normal saline solution should be used to prime the balloon and it's inflation channel. All air should be removed from the balloon and inflation channel by aspiration of fluid from balloon and channel. After priming and removal of air the stopcock valve to the balloon inflation channel should be closed leaving the balloon collapsed around the main body of the cathether (see FIGS. 9, 10A and 10B for diagram of port, lumen and component locations). To avoid potential over-inflation, less than 35 cubic centimeters (cc) of solution should be reserved in the inflation syringe(s) for balloon inflation. The catheter of this invention (with the obturator) inserted is placed to the side for later insertion.

If Fluoroscopic visualization of the catheter and balloon inflation is desired, a dilute intravenous contrast solution (10% CONRAY® or equivalent), diluted to a total of approximately 2% contrast, should be prepared and used to prime the balloon and its inflation channel.
4. The common femoral artery on the side selected for introduction of the cannula is surgically exposed, obtaining proximal and distal control of the vessel and any significant branches.
5. The patient is systemically anticoagulated as appropriate for cardiopulmonary bypass using heparin administered intravenously, with activated clotting times (ACT) determined in the routine fashion. The catheter of the invention with hollow-needle obturator is inserted into the femoral artery, with free blood return verifying intralumenal tip location. The needle obturator is removed, and a 0.035× 180 cm stiff guide wire is introduced through the cannula and advanced cephalad up the aorta and across the aortic arch to position the tip in the ascending aorta. TEE imaging should be used to verify proper guide wire placement in the ascending aorta. Fluoroscopic visualization of the guide wire placement may also be used if desired.
6. During brief occlusion of the femoral artery the short femoral cannula is removed and a 1 cm transverse arteriotomy is created encompassing the site of the wire entry across the anterior arterial wall. The 0.035×180 cm Guide wire is back fed into the aortic root (for cardioplegia) of the catheter and through the hemostatic valve that comes attached to the lumen (see FIGS. 9, 10A and 10B for diagram of port, lumen and component locations). The valve is adjusted by tightening the thumbscrew of the hemostatic valve. The valve is tightened as much as possible while still allowing the guide wire to move freely through the valve. The guide wire is left in position until the catheter insertion is completed. Use of a soft-jaw clamp to control blood loss at femoral artery insertion site is recommended.
7. The catheter is advanced over the guide wire into the femoral artery through the short sheath. The catheter (with obturator) is advanced in a retrograde fashion up the lilac artery, abdominal aorta and thoracic aorta. The catheter is guided over the aortic arch with imaging assistance and the tip of the catheter is advanced into the ascending aorta. The position of the tip should be evaluated using TEE to verify that the tip is above and not interfering with the aortic valve. If fluoroscopic visualization is desired, the radiopaque marker at the tip of the catheter can be used to assist placement. This will position the occlusion balloon in the ascending aorta, proximal to the origin of the innominate artery. In open sternotomy applications, tip position may be verified by direct palpation of the aortic root. The obturator is removed from the catheter, which is de-aired by allowing back bleeding, and then clamped at the ⅜ tubing area provided for clamping (see 113 of FIGS. 9, 10A and 10B for diagram of port, lumen and component locations). The obturator should be appropriately set aside for reinsertion, if required.
8. The blood flow lumen of the catheter is attached at port 108 (see FIG. 9, 10A and 10B) to the arterial blood supply line from the CPB machine, taking care not to introduce air at the site of connection.

9. The inflation syringe filled with saline solution is attached via three-way valved manifold (stopcock) to the occlusion balloon control lumen. A pressure line from a suitable pressure monitoring device should be attached to the remaining valve port to monitor balloon inflation die pressure (see FIGS. 9, 10A and 10B for diagram of port, lumen and component locations).
10. The aortic root lumen is attached via three-way valved manifold (stopcock) to the cardioplegia solution delivery/vent line from the CPB machine. Pressure line from suitable pressure monitoring device should be attached to remaining valve port 111 to monitor cardioplegia or aortic root pressure. The cardiopulmonary bypass machine vent line must be equipped with a ventricular vent valve to prevent excessive negative pressure on the vent line (see FIGS. 9, 10A and 10B for diagram of port, lumen and component locations).
11. Cardioplegic solution line pressure, aortic root pressure, and balloon inflation pressure are measured at the appropriate ports as indicated (see FIGS. 9, 10A, 10B for diagram of port, lumen and component locations).
12. Venous cannulation is performed by direct cannulation of the right atrium with a single or dual-stage cannula, selected cannulation of the superior and inferior vena cavas, or cannulation of the right atrium via the femoral, jugular or subclavian vein.
13. Cardiopulmonary bypass is initiated.
14. When aortic occlusion is required, the CPB blood flow is momentarily reduced to 25% and using the inflation syringe, the balloon is inated to contact the vessel wall. After initial contact, under careful EE monitoring (Fluoroscopic visualization of balloon inflation may also be used if desired). An additional fluid should be added slowly until appropriate occlusion and stability are achieved. Inflation volume of 35 cc or balloon pressure of 400 mmHg should not be exceeded. Full blood flow rate is then resumed. A volume of 10 cc will result in a balloon diameter of 25–26 mm.

Inappropriate venous drainage may cause the heart to eject against the balloon during inflation, resulting in balloon movement during inflation.

The right and left radial/brachial pressure waveforms and arterial waveforms are closely monitored and evaluated continuously during the period of balloon inflation, and the position of the balloon observed with TEE. Any change in the right radial/brachial waveform (in comparison to the left) may indicate that the occlusion balloon is obstructing the origin of the innominate artery, requiring deflation and repositioning.
15. Cardioplegic solution is administered through the aortic root line 109 as required to provide arrest. Prior to the delivery of cardioplegia, the aortic vent should be stopped for 1–2 minutes to allow accumulation of blood at the aortic root. The aortic root lumen is then cleared of air by gentle aspiration or gravity blood flow back through the lumen, then the cardioplegia solution can be administered through the lumen. The cardioplegia flow should begin slowly, and gradually be increased to the desired flow and pressure. The position of the occluding balloon should be closely observed for shifts during the delivery of cardioplegia, and verified again after cessation of the cardioplegia delivery.
16. The aortic root lumen may be opened to the CPB vent line when cardioplegia is not being administered. A safety valve should be inserted into the vent line to prevent more than 80 mmHg of vacuum. It is recommended that the surgical field be flushed with $CO_2$ to prevent air introduction.
17. When aortic occlusion is no longer required, fluid from the balloon should be gently aspirated until the total volume used for inflation is returned to the syringe. The stopcock to the balloon inflation lumen should be closed to assure the balloon is collapsed against the catheter. The catheter may now be withdrawn at the conclusion of the bypass.
18. To remove the catheter after conclusion of bypass, the catheter is withdrawn to indicator mark indicating distal blood outlet port is two inches from arterial access incision, clamp cannula at indicator mark using tube-occluding forceps. A sterile towel should be wrapped around the catheter covering exposed portion of catheter between indicator mark and distal end of catheter. This will provide controlled blood loss during cannula withdrawal. If obturator reinsertion is desired, obturator may now be inserted back into cathether up to position of clamp. Clamp should be removed and obturator advanced to incision site. The catheter (with obturator) can now be withdrawn and access incision closed.

Should change out of the catheter be required during cardiopulmonary bypass, the following steps are followed. This is a representative process for using the catheter of this invention given as a stepwise approach.
1. Completely deflate occlusion balloon.
2. Insert 0.035×180-cm stiff guide wire through hemostatic valve attached to aortic root lumen, adjust valve to control bleed-back while still allowing free movement of guide wire. Use TEE and/or fluoroscopic imaging to position tip of guide wire in ascending aorta at tip of aortic cannula.
3. Prepare new catheter for introduction as specified in directions for use in step 3, above.
4. Discontinue arterial blood flow from cardiopulmonary bypass machine.
5. Clamp catheter at ⅜ tubing section provided for clamping. Clamp cardiopulmonary bypass machine arterial line just distal of the catheter connection. Separate connection between the catheter and cardiopulmonary bypass machine arterial line.
6. Withdraw catheter over guide wire and remove it from guide wire taking care not to change position of guide wire in aorta. Use of a soft-jaw clamp to control blood loss at femoral artery insertion site is recommended.
7. Advance new catheter over guide wire, balloon first into the femoral artery. The catheter (with obturator) is advanced in a retrograde fashion up the lilac artery, abdominal aorta and thoracic aorta. When the catheter has been advanced past the indicator markers, the obturator can be removed from the catheter, which is de-aired by allowing back bleeding, and then clamped at the ⅜ tubing area provided for clamping. The cardiopulmonary bypass machine arterial line may now be connected to the catheter, taking care not to introduce any air into the line while connecting. Bypass may now be reinitiated.

The catheter of this invention should then be positioned and used as referred to in directions for use for steps number 7 through 18, above.

All references to any patents or articles in this application are to be interpreted to specially incorporate each in this application by reference.

What is claimed is:

1. A process for preparing for cardiovascular surgery in a mammal, which process comprises
   (A) providing a multichannel catheter useful for delivering extracorporeal blood to a mammal in need thereof by insertion into a blood vessel of the mammal, which catheter has a defined length with distal and proximal ends and comprises:

a central, first channel defined by a surrounding wall extending substantially the length of the catheter, which channel is closed at its distal end:

a second channel (i) extending substantially the length of the catheter parallel to the first channel but independent thereof, (ii) being integrated into the wall of the first channel, and (iii) being open at its distal end:

a plurality of openings for the outflow of blood in the wall of the catheter communicating only with said first channel:

an inflatable bladder integrated into the distal end of the catheter between the openings for the outflow of blood and the second channel distal opening;

a third channel (i) extending substantially the length of said catheter integrated into the wall of the first channel: (ii) being parallel to the first and second channels but independent thereof, and (iii) having a distal opening in fluid communication with the interior of the inflatable bladder, and a solid flexible shaft slidably engageable into the first channel extending substantially the length of the first channel:

(B) inserting into a femoral artery of the mammal the distal end of the catheter with the flexible shaft slidingly engaged in the first channel to prevent backflow of blood, (C) positioning the catheter so that the inflatable bladder is located in the ascending aorta, and (D) removing the flexible shaft from the first channel to allow the first channel to be connected to a cardiopulmonary machine to pump blood into the first channel at the proximal end of the first channel.

2. The process of claim 1, which further comprises (E) inserting at least one cannula into a mammal's peripheral veins to position it so the distal open end of the cannula is adjacent the vena cava regions of the mammal's heart and the proximal end of the cannula is attached to a cardiopulmonary machine through a pump wherein the cardiopulmonary machine comprises a blood oxygenation means fluidly connected to the pump, (F) providing a source of oxygenated blood from the cardiopulmonary machine to the proximal end of the first channel;

(G) providing a source of cardioplegia fluid to the proximal end of the second channel in an amount sufficient to reach the coronary arteries and reduce the heart rate;

(H) providing a source of fluid for inflating the inflatable bladder to the proximal end of said third channel to inflate the inflatable bladder to block the flow of blood to the heart;

(I) pumping oxygen-rich blood through the first channel and out the first channel openings at a rate sufficient to maintain the mammal's metabolism and perfusion; and (J) removing oxygen-depleted blood from the mammal's vena cavae regions through the femoral vein cannula.

3. The process of claim 2 that further comprises performing cardiovascular surgery as needed and continuing to pump the oxygen-rich blood to the mammal at a rate sufficient to maintain the mammal's metabolism and perfusion.

* * * * *